US008227362B2

(12) United States Patent
Haile et al.

(10) Patent No.: US 8,227,362 B2
(45) Date of Patent: *Jul. 24, 2012

(54) WATER-DISPERSIBLE AND MULTICOMPONENT FIBERS FROM SULFOPOLYESTERS

(75) Inventors: William Alston Haile, Kingsport, TN (US); Scott Ellery George, Kingsport, TN (US); Wesley Raymond Hale, Kingsport, TN (US); Waylon Lewellyn Jenkins, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/966,502

(22) Filed: Dec. 13, 2010

(65) Prior Publication Data

US 2011/0142896 A1    Jun. 16, 2011

Related U.S. Application Data

(60) Continuation of application No. 11/204,868, filed on Aug. 16, 2005, now Pat. No. 7,902,094, which is a division of application No. 10/850,548, filed on May 20, 2004, now Pat. No. 6,989,193, which is a continuation-in-part of application No. 10/465,698, filed on Jun. 19, 2003, now abandoned.

(51) Int. Cl.
*D04H 3/16* (2006.01)
*D04H 13/00* (2006.01)
*D04H 1/46* (2006.01)

(52) U.S. Cl. ........ 442/363; 442/361; 442/362; 442/364; 442/400; 442/401

(58) Field of Classification Search .......... 442/361–364, 442/400–401
See application file for complete search history.

(56) References Cited

U.S. PATENT DOCUMENTS

| | | | |
|---|---|---|---|
| 3,018,272 A | 1/1962 | Griffing et al. |
| 3,033,822 A | 5/1962 | Kibler et al. |
| 3,049,469 A | 8/1962 | Davison et al. |
| 3,075,952 A | 1/1963 | Coover et al. |
| 3,528,947 A | 9/1970 | Lappin et al. |
| 3,556,932 A | 1/1971 | Coscia et al. |
| 3,592,796 A | 7/1971 | Trapasso et al. |
| 3,772,076 A | 11/1973 | Keim |
| 3,779,993 A | 12/1973 | Kibler et al. |
| 3,783,093 A | 1/1974 | Gallacher et al. |
| 3,803,210 A | 4/1974 | Rod et al. |
| 3,833,457 A | 9/1974 | Misumi et al. |
| 3,846,507 A | 11/1974 | Thomm et al. |
| 3,998,740 A | 12/1976 | Bost et al. |
| 4,008,344 A | 2/1977 | Okamoto et al. |
| 4,073,777 A | 2/1978 | O'Neill et al. |
| 4,073,988 A | 2/1978 | Nishida et al. |
| 4,100,324 A | 7/1978 | Anderson et al. |
| 4,104,262 A | 8/1978 | Schade |
| 4,121,966 A | 10/1978 | Amano et al. |
| 4,127,696 A | 11/1978 | Okamoto |
| 4,137,393 A | 1/1979 | Sidebotham et al. |
| 4,145,469 A | 3/1979 | Newkirk et al. |
| 4,233,355 A | 11/1980 | Sato et al. |
| 4,234,652 A | 11/1980 | Vanoni et al. |
| 4,239,720 A | 12/1980 | Gerlach et al. |
| 4,240,918 A | 12/1980 | Lagasse et al. |
| 4,297,412 A | 10/1981 | Achard et al. |
| 4,299,654 A | 11/1981 | Tlach et al. |
| 4,302,495 A | 11/1981 | Marra |
| 4,304,901 A | 12/1981 | O'Neill et al. |
| 4,342,801 A | 8/1982 | Gerlach et al. |
| 4,350,006 A | 9/1982 | Okamoto et al. |
| 4,365,041 A | 12/1982 | Okamoto et al. |
| 4,381,335 A | 4/1983 | Okamoto |
| 4,410,579 A | 10/1983 | Johns |
| 4,427,557 A | 1/1984 | Stockburger |
| 4,460,649 A | 7/1984 | Park et al. |
| 4,496,619 A | 1/1985 | Okamoto |
| 4,517,715 A | 5/1985 | Yoshida et al. |
| 4,618,524 A | 10/1986 | Groitzsch et al. |

(Continued)

FOREIGN PATENT DOCUMENTS

| | | |
|---|---|---|
| CA | 1290517 | 10/1991 |
| EP | 0340763 A1 | 11/1989 |
| EP | 0610894 A1 | 8/1994 |
| EP | 0610897 | 8/1994 |
| EP | 0 666 344 B1 | 9/1999 |
| EP | 1 243 675 A1 | 9/2002 |
| EP | 0 645 480 B1 | 11/2002 |
| EP | 0 961 847 B1 | 12/2002 |
| EP | 1359632 A2 | 4/2003 |
| EP | 0 935 682 B1 | 9/2003 |

(Continued)

OTHER PUBLICATIONS

Polymer Blends, vols. 1 and 2, Edited by D. R. Paul and C. B. Bucknell, 2000, John Wiley & Sons, Inc.

(Continued)

*Primary Examiner* — Lynda Salvatore
(74) *Attorney, Agent, or Firm* — Polly C. Owen

(57) ABSTRACT

Disclosed are water-dispersible fibers derived from sulfopolyesters having a Tg of at least 25° C. The fibers may contain a single sulfopolyester or a blend of a sulfopolyester with a water-dispersible or water-nondispersible polymer. Also disclosed are multicomponent fibers comprising a water dispersible sulfopolyester having a Tg of at least 57° C. and a water non-dispersible polymer. The multicomponent fibers may be used to produce microdenier fibers. Fibrous articles may be produced from the water-dispersible fibers, multicomponent fibers, and microdenier fibers. The fibrous articles include water-dispersible and microdenier nonwoven webs, fabrics, and multilayered articles such as wipes, gauze, tissue, diapers, panty liners, sanitary napkins, bandages, and surgical dressings. Also disclosed is a process for water-dispersible fibers, nonwoven fabrics, and microdenier webs. The fibers and fibrous articles have further applications in flushable personal care and cleaning products, disposable protective outerwear, and laminating binders.

38 Claims, No Drawings

U.S. PATENT DOCUMENTS

| | | |
|---|---|---|
| 4,699,845 A | 10/1987 | Oikawa et al. |
| 4,738,785 A | 4/1988 | Langston et al. |
| 4,755,421 A | 7/1988 | Manning et al. |
| 4,795,668 A | 1/1989 | Krueger et al. |
| 4,804,719 A | 2/1989 | Weaver et al. |
| 4,810,775 A | 3/1989 | Bendix et al. |
| 4,863,785 A | 9/1989 | Berman et al. |
| 4,910,292 A | 3/1990 | Blount |
| 4,921,899 A | 5/1990 | Phan et al. |
| 4,940,744 A | 7/1990 | Tortorici et al. |
| 4,946,932 A | 8/1990 | Jenkins |
| 4,966,808 A | 10/1990 | Kawano |
| 4,973,656 A | 11/1990 | Blount |
| 4,990,593 A | 2/1991 | Blount |
| 4,996,252 A | 2/1991 | Phan et al. |
| 5,006,598 A | 4/1991 | Adams et al. |
| 5,039,339 A | 8/1991 | Phan et al. |
| 5,057,368 A | 10/1991 | Largman et al. |
| 5,069,970 A | 12/1991 | Largman et al. |
| 5,073,436 A | 12/1991 | Antonacci et al. |
| 5,108,820 A | 4/1992 | Kaneko et al. |
| 5,124,194 A | 6/1992 | Kawano |
| 5,162,074 A | 11/1992 | Hills |
| 5,162,399 A | 11/1992 | Sharma et al. |
| 5,171,767 A | 12/1992 | Buckley et al. |
| 5,176,952 A | 1/1993 | Joseph et al. |
| 5,218,042 A | 6/1993 | Kuo et al. |
| 5,242,640 A | 9/1993 | Butler et al. |
| 5,258,220 A | 11/1993 | Joseph |
| 5,262,460 A | 11/1993 | Suzuki et al. |
| 5,274,025 A | 12/1993 | Stockl et al. |
| 5,277,976 A | 1/1994 | Hogle et al. |
| 5,281,306 A | 1/1994 | Kakiuchi et al. |
| 5,286,843 A | 2/1994 | Wood |
| 5,290,626 A | 3/1994 | Nishioi et al. |
| 5,290,631 A | 3/1994 | Fleury et al. |
| 5,290,654 A | 3/1994 | Sacripante et al. |
| 5,292,581 A | 3/1994 | Viazmensky et al. |
| 5,292,855 A | 3/1994 | Krutak et al. |
| 5,308,697 A | 5/1994 | Muramoto et al. |
| 5,336,552 A | 8/1994 | Strack et al. |
| 5,338,406 A | 8/1994 | Smith |
| 5,342,863 A | 8/1994 | Buckley et al. |
| 5,366,804 A | 11/1994 | Dugan |
| 5,368,928 A | 11/1994 | Okamura et al. |
| 5,369,210 A | 11/1994 | George et al. |
| 5,369,211 A | 11/1994 | George et al. |
| 5,374,357 A | 12/1994 | Comstock et al. |
| 5,375,306 A | 12/1994 | Roussin-Moynier |
| 5,378,757 A | 1/1995 | Blount, Jr. et al. |
| 5,382,400 A | 1/1995 | Pike et al. |
| 5,386,003 A | 1/1995 | Greene et al. |
| 5,389,068 A | 2/1995 | Keck |
| 5,395,693 A | 3/1995 | Cho et al. |
| 5,405,698 A | 4/1995 | Dugan |
| 5,423,432 A | 6/1995 | Krutak et al. |
| 5,446,079 A | 8/1995 | Buchanan et al. |
| 5,456,982 A | 10/1995 | Hansen et al. |
| 5,466,410 A | 11/1995 | Hills |
| 5,466,518 A | 11/1995 | Isaac et al. |
| 5,472,600 A | 12/1995 | Ellefson et al. |
| 5,482,772 A | 1/1996 | Strack et al. |
| 5,486,418 A | 1/1996 | Ohmory et al. |
| 5,502,091 A | 3/1996 | Dasgupta |
| 5,508,101 A | 4/1996 | Patnode et al. |
| 5,509,913 A | 4/1996 | Yeo |
| 5,525,282 A | 6/1996 | Dugan |
| 5,530,059 A | 6/1996 | Blount, Jr. et al. |
| 5,536,811 A | 7/1996 | Wood |
| 5,543,488 A | 8/1996 | Miller et al. |
| 5,545,481 A | 8/1996 | Harrington |
| 5,552,495 A | 9/1996 | Miller et al. |
| 5,559,171 A | 9/1996 | Buchanan et al. |
| 5,559,205 A | 9/1996 | Hansen et al. |
| 5,567,510 A | 10/1996 | Patnode et al. |
| 5,571,620 A | 11/1996 | George et al. |
| 5,575,918 A | 11/1996 | Virnig et al. |
| 5,580,911 A | 12/1996 | Buchanan et al. |
| 5,593,778 A | 1/1997 | Kondo et al. |
| 5,593,807 A | 1/1997 | Sacripante et al. |
| 5,599,858 A | 2/1997 | Buchanan et al. |
| 5,605,746 A | 2/1997 | Groeger et al. |
| 5,607,491 A | 3/1997 | Jackson et al. |
| 5,607,765 A | 3/1997 | Hansen et al. |
| 5,620,785 A | 4/1997 | Watt et al. |
| 5,630,972 A | 5/1997 | Patnode et al. |
| 5,635,071 A | 6/1997 | Al-Samadi |
| 5,637,385 A | 6/1997 | Mizuki et al. |
| 5,643,662 A | 7/1997 | Yeo et al. |
| 5,646,237 A | 7/1997 | George et al. |
| 5,652,048 A | 7/1997 | Haynes et al. |
| 5,654,086 A | 8/1997 | Nishijima et al. |
| 5,658,704 A | 8/1997 | Patel et al. |
| 5,660,965 A | 8/1997 | Mychajlowskij et al. |
| 5,672,415 A | 9/1997 | Sawyer et al. |
| 5,688,582 A | 11/1997 | Nagaoka et al. |
| 5,698,331 A | 12/1997 | Matsumura et al. |
| 5,709,940 A | 1/1998 | George et al. |
| 5,736,083 A | 4/1998 | Dugan |
| 5,750,605 A | 5/1998 | Blumenthal et al. |
| 5,753,351 A | 5/1998 | Yoshida et al. |
| 5,759,926 A | 6/1998 | Pike et al. |
| 5,763,065 A | 6/1998 | Patnode et al. |
| 5,798,078 A | 8/1998 | Myers |
| 5,817,740 A | 10/1998 | Anderson et al. |
| 5,820,982 A | 10/1998 | Salsman |
| 5,853,701 A | 12/1998 | George et al. |
| 5,853,944 A | 12/1998 | Foucher et al. |
| 5,883,181 A | 3/1999 | Cicchiello et al. |
| 5,888,916 A | 3/1999 | Tadokoro et al. |
| 5,895,710 A | 4/1999 | Sasse et al. |
| 5,916,678 A * | 6/1999 | Jackson et al. ............... 428/373 |
| 5,916,687 A | 6/1999 | Takanashi et al. |
| 5,916,725 A | 6/1999 | Patel et al. |
| 5,916,935 A | 6/1999 | Wiggins et al. |
| 5,935,880 A | 8/1999 | Wang et al. |
| 5,935,883 A | 8/1999 | Pike |
| 5,948,710 A | 9/1999 | Pomplun et al. |
| 5,952,251 A | 9/1999 | Jackson et al. |
| 5,954,967 A | 9/1999 | Egraz et al. |
| 5,970,583 A | 10/1999 | Groten et al. |
| 5,976,694 A | 11/1999 | Tsai et al. |
| 5,993,668 A | 11/1999 | Duan |
| 5,993,834 A | 11/1999 | Shah et al. |
| 6,004,673 A | 12/1999 | Nishijima |
| 6,007,910 A | 12/1999 | Miller et al. |
| 6,020,420 A | 2/2000 | George |
| 6,037,055 A | 3/2000 | Aneja et al. |
| 6,057,388 A | 5/2000 | Wiggins et al. |
| 6,080,471 A | 6/2000 | Shigematsu et al. |
| 6,090,731 A | 7/2000 | Pike et al. |
| 6,110,588 A | 8/2000 | Perez et al. |
| 6,110,636 A | 8/2000 | Foucher et al. |
| 6,114,407 A | 9/2000 | Myers |
| 6,120,889 A | 9/2000 | Turner et al. |
| 6,121,170 A | 9/2000 | Tsai et al. |
| 6,162,340 A | 12/2000 | Zakikhani |
| 6,162,890 A | 12/2000 | George et al. |
| 6,168,719 B1 | 1/2001 | Shimokawa et al. |
| 6,171,685 B1 * | 1/2001 | George et al. ............... 428/221 |
| 6,174,602 B1 | 1/2001 | Matsui et al. |
| 6,177,193 B1 | 1/2001 | Tsai et al. |
| 6,177,607 B1 | 1/2001 | Blaney et al. |
| 6,183,648 B1 | 2/2001 | Kozak et al. |
| 6,211,309 B1 | 4/2001 | McIntosh et al. |
| 6,218,321 B1 | 4/2001 | Lorcks et al. |
| 6,225,243 B1 | 5/2001 | Austin |
| 6,248,809 B1 | 6/2001 | Buckley et al. |
| 6,294,645 B1 | 9/2001 | Allen et al. |
| 6,296,933 B1 | 10/2001 | Goda et al. |
| 6,300,306 B1 | 10/2001 | Firkins et al. |
| 6,316,592 B1 | 11/2001 | Bates et al. |
| 6,322,887 B1 | 11/2001 | Matsui et al. |
| 6,331,606 B1 | 12/2001 | Sun |
| 6,332,994 B1 | 12/2001 | Karageorgiou |
| 6,348,679 B1 | 2/2002 | Ryan et al. |
| 6,352,948 B1 | 3/2002 | Pike et al. |

| Patent No. | Date | Inventor(s) |
|---|---|---|
| 6,355,137 B1 | 3/2002 | Staib |
| 6,361,784 B1 * | 3/2002 | Brennan et al. ............... 424/402 |
| 6,365,697 B1 | 4/2002 | Kim et al. |
| 6,369,136 B2 | 4/2002 | Sorriero et al. |
| 6,381,817 B1 | 5/2002 | Moody, III |
| 6,402,870 B1 | 6/2002 | Groten et al. |
| 6,403,677 B1 | 6/2002 | Walker |
| 6,417,251 B1 | 7/2002 | Brady |
| 6,420,024 B1 | 7/2002 | Perez et al. |
| 6,420,027 B2 | 7/2002 | Kimura et al. |
| 6,428,900 B1 | 8/2002 | Wang |
| 6,430,348 B1 | 8/2002 | Asano et al. |
| 6,432,532 B2 | 8/2002 | Perez et al. |
| 6,436,855 B1 | 8/2002 | Iwata et al. |
| 6,440,556 B2 | 8/2002 | Matsui et al. |
| 6,488,731 B2 | 12/2002 | Schultheiss et al. |
| 6,506,853 B2 | 1/2003 | Duan |
| 6,509,092 B1 | 1/2003 | Dugan |
| 6,512,024 B1 | 1/2003 | Lundgard et al. |
| 6,533,938 B1 | 3/2003 | Dilorio et al. |
| 6,541,175 B1 | 4/2003 | Jiang et al. |
| 6,548,592 B1 | 4/2003 | Lang et al. |
| 6,550,622 B2 | 4/2003 | Koslow |
| 6,551,353 B1 | 4/2003 | Baker et al. |
| 6,552,123 B1 | 4/2003 | Katayama et al. |
| 6,552,162 B1 | 4/2003 | Wang et al. |
| 6,554,881 B1 | 4/2003 | Healey |
| 6,573,204 B1 | 6/2003 | Philipp et al. |
| 6,576,716 B1 | 6/2003 | Wo |
| 6,579,466 B1 | 6/2003 | David et al. |
| 6,583,075 B1 | 6/2003 | Dugan |
| 6,586,529 B2 | 7/2003 | Mumick et al. |
| 6,589,426 B1 | 7/2003 | Husain et al. |
| 6,602,955 B2 | 8/2003 | Soerens et al. |
| H002086 H | 10/2003 | Amsler |
| 6,638,677 B2 | 10/2003 | Patel et al. |
| 6,657,017 B2 | 12/2003 | Wo et al. |
| 6,664,437 B2 | 12/2003 | Sawyer et al. |
| 6,692,825 B2 | 2/2004 | Qin et al. |
| 6,706,652 B2 | 3/2004 | Groten et al. |
| 6,730,387 B2 | 5/2004 | Rezai et al. |
| 6,743,506 B2 | 6/2004 | Bond et al. |
| 6,746,766 B2 | 6/2004 | Bond et al. |
| 6,746,779 B2 | 6/2004 | Hayes et al. |
| 6,759,124 B2 | 7/2004 | Royer et al. |
| 6,764,802 B2 | 7/2004 | Maric et al. |
| 6,767,498 B1 | 7/2004 | Talley, Jr. et al. |
| 6,776,858 B2 | 8/2004 | Bansal et al. |
| 6,780,560 B2 | 8/2004 | Farrugia et al. |
| 6,780,942 B2 | 8/2004 | Leon et al. |
| 6,815,382 B1 | 11/2004 | Groten et al. |
| 6,838,172 B2 | 1/2005 | Yoon et al. |
| 6,838,403 B2 | 1/2005 | Tsai et al. |
| 6,844,062 B2 | 1/2005 | Matsui et al. |
| 6,844,063 B2 | 1/2005 | Matsui et al. |
| 6,849,329 B2 | 2/2005 | Perez et al. |
| 6,855,422 B2 | 2/2005 | Magill et al. |
| 6,860,906 B2 | 3/2005 | Malisz et al. |
| 6,861,142 B1 | 3/2005 | Wilkie et al. |
| 6,890,649 B2 | 5/2005 | Hobbs et al. |
| 6,893,711 B2 | 5/2005 | Williamson et al. |
| 6,900,148 B2 | 5/2005 | Yoneda et al. |
| 6,902,796 B2 | 6/2005 | Morell et al. |
| 6,946,506 B2 | 9/2005 | Bond et al. |
| 6,949,288 B2 | 9/2005 | Hodge et al. |
| 6,953,622 B2 | 10/2005 | Tsai et al. |
| 6,989,193 B2 | 1/2006 | Haile et al. |
| 6,989,194 B2 | 1/2006 | Bansal et al. |
| 7,008,485 B2 | 3/2006 | Heikkila et al. |
| 7,011,653 B2 | 3/2006 | Imsangjan et al. |
| 7,011,885 B2 | 3/2006 | Chang et al. |
| 7,014,803 B2 | 3/2006 | Perez et al. |
| 7,022,201 B2 | 4/2006 | Anderson et al. |
| 7,025,885 B2 | 4/2006 | Cote et al. |
| 7,026,033 B2 | 4/2006 | Fujimori et al. |
| 7,070,695 B2 | 7/2006 | Husain et al. |
| 7,087,301 B2 | 8/2006 | Musgrave et al. |
| 7,091,140 B1 | 8/2006 | Ferencz et al. |
| 7,097,904 B2 | 8/2006 | Ochi et al. |
| 7,144,614 B2 | 12/2006 | Nakajima et al. |
| 7,160,612 B2 | 1/2007 | Magill et al. |
| 7,163,744 B2 | 1/2007 | Nightingale et al. |
| 7,166,225 B2 | 1/2007 | Pitt et al. |
| 7,179,376 B2 | 2/2007 | Kaleem et al. |
| 7,186,343 B2 | 3/2007 | Rabie et al. |
| 7,186,344 B2 | 3/2007 | Hughes |
| 7,193,029 B2 | 3/2007 | Hayes |
| 7,194,788 B2 | 3/2007 | Clark et al. |
| 7,195,814 B2 | 3/2007 | Ista et al. |
| 7,214,765 B2 | 5/2007 | Ringeisen et al. |
| 7,220,815 B2 | 5/2007 | Hayes |
| 7,238,415 B2 | 7/2007 | Rodriguez et al. |
| 7,238,423 B2 | 7/2007 | Calhoun et al. |
| 7,241,497 B2 | 7/2007 | Magill et al. |
| 7,276,139 B2 | 10/2007 | Katai et al. |
| 7,285,209 B2 | 10/2007 | Yu et al. |
| 7,291,270 B2 | 11/2007 | Gibson et al. |
| 7,291,389 B1 | 11/2007 | Bitler et al. |
| 7,304,125 B2 | 12/2007 | Ibar |
| 7,306,735 B2 | 12/2007 | Baggott et al. |
| 7,309,372 B2 | 12/2007 | Kahlbaugh et al. |
| 7,314,497 B2 | 1/2008 | Kahlbaugh et al. |
| 7,329,723 B2 | 2/2008 | Jernigan et al. |
| 7,338,664 B2 | 3/2008 | Tseng et al. |
| 7,344,775 B2 | 3/2008 | Stevens et al. |
| 7,347,947 B2 | 3/2008 | Nakamura et al. |
| 7,357,985 B2 | 4/2008 | Kurian et al. |
| 7,358,022 B2 | 4/2008 | Farrugia et al. |
| 7,358,323 B2 | 4/2008 | Maeda et al. |
| 7,358,325 B2 | 4/2008 | Hayes |
| 7,361,700 B2 | 4/2008 | Sunamori et al. |
| 7,365,118 B2 | 4/2008 | McCleskey et al. |
| 7,371,701 B2 | 5/2008 | Inagaki |
| 7,387,976 B2 | 6/2008 | Baba et al. |
| 7,388,058 B2 | 6/2008 | Kaku et al. |
| 7,405,171 B2 | 7/2008 | Tsujiyama et al. |
| 7,405,266 B2 | 7/2008 | Bentley et al. |
| 7,432,219 B2 | 10/2008 | Strandqvist et al. |
| 7,442,277 B2 | 10/2008 | Kupper et al. |
| 7,462,386 B2 | 12/2008 | Yamasaki et al. |
| 7,497,895 B2 | 3/2009 | Sabottke |
| 7,513,004 B2 | 4/2009 | Luckman et al. |
| 7,560,159 B2 | 7/2009 | Goda et al. |
| 7,576,019 B2 | 8/2009 | Bond et al. |
| 7,588,688 B2 | 9/2009 | Butters et al. |
| 7,622,188 B2 | 11/2009 | Kamiyama et al. |
| 7,655,070 B1 | 2/2010 | Dallas et al. |
| 7,666,500 B2 | 2/2010 | Magill et al. |
| 7,666,502 B2 | 2/2010 | Magill et al. |
| 7,666,504 B2 | 2/2010 | Ochi et al. |
| 7,687,143 B2 | 3/2010 | Gupta et al. |
| 7,695,812 B2 | 4/2010 | Peng et al. |
| 7,696,111 B2 | 4/2010 | Mangold et al. |
| 7,704,595 B2 | 4/2010 | Morin |
| 7,718,104 B2 | 5/2010 | MacDonald et al. |
| 7,727,627 B2 | 6/2010 | Sen et al. |
| 7,732,557 B2 | 6/2010 | Phelps et al. |
| 7,736,737 B2 | 6/2010 | Van Dun et al. |
| 7,737,060 B2 | 6/2010 | Strickler et al. |
| 7,744,807 B2 | 6/2010 | Berrigan et al. |
| 7,754,123 B2 | 7/2010 | Verdegan et al. |
| 7,757,811 B2 | 7/2010 | Fox et al. |
| 7,765,647 B2 | 8/2010 | Smith et al. |
| 7,772,456 B2 | 8/2010 | Zhang et al. |
| 7,820,568 B2 | 10/2010 | Horiguchi et al. |
| 7,837,814 B2 | 11/2010 | Minami et al. |
| 7,858,732 B2 | 12/2010 | Bruchmann et al. |
| 7,883,604 B2 | 2/2011 | Dyer et al. |
| 7,884,037 B2 | 2/2011 | Sirovatka et al. |
| 7,887,526 B2 | 2/2011 | Van Gompel et al. |
| 7,892,672 B2 | 2/2011 | Nishikawa |
| 7,892,992 B2 | 2/2011 | Kamada et al. |
| 7,896,940 B2 | 3/2011 | Sundet et al. |
| 7,897,078 B2 | 3/2011 | Petersen et al. |
| 7,897,248 B2 | 3/2011 | Barrera et al. |
| 7,902,094 B2 | 3/2011 | Haile et al. |
| 7,902,096 B2 | 3/2011 | Brandner et al. |
| 7,910,207 B2 | 3/2011 | Kamiyama et al. |

| | | |
|---|---|---|
| 7,914,866 B2 | 3/2011 | Shannon et al. |
| 7,918,313 B2 | 4/2011 | Gross et al. |
| 7,919,419 B2 | 4/2011 | Hurley et al. |
| 7,922,959 B2 | 4/2011 | Jones et al. |
| 7,923,143 B2 | 4/2011 | Tanaka et al. |
| 7,928,025 B2 | 4/2011 | Shipley et al. |
| 7,931,457 B2 | 4/2011 | Johnson et al. |
| 7,932,192 B2 | 4/2011 | Fujisawa et al. |
| 7,935,645 B2 | 5/2011 | Pourdeyhimi et al. |
| 7,947,142 B2 | 5/2011 | Fox et al. |
| 7,947,864 B2 | 5/2011 | Damay et al. |
| 7,951,313 B2 | 5/2011 | Matsubayashi et al. |
| 7,951,452 B2 | 5/2011 | Nakayama et al. |
| 7,959,848 B2 | 6/2011 | Reneker et al. |
| 2002/0009590 A1 | 1/2002 | Matsui et al. |
| 2002/0030016 A1 | 3/2002 | Schmidt |
| 2002/0079121 A1 | 6/2002 | Ryan et al. |
| 2002/0123290 A1 | 9/2002 | Tsai et al. |
| 2002/0127937 A1 | 9/2002 | Lange et al. |
| 2002/0127939 A1 | 9/2002 | Hwo et al. |
| 2002/0146552 A1 | 10/2002 | Mumick et al. |
| 2002/0187329 A1 | 12/2002 | Ista et al. |
| 2003/0026986 A1 | 2/2003 | Matsui et al. |
| 2003/0057155 A1 | 3/2003 | Husain et al. |
| 2003/0077444 A1 | 4/2003 | Bond et al. |
| 2003/0091822 A1 | 5/2003 | Bond et al. |
| 2003/0092343 A1 | 5/2003 | Bond et al. |
| 2003/0104204 A1 | 6/2003 | Bond et al. |
| 2003/0111763 A1 | 6/2003 | Jen |
| 2003/0166370 A1 | 9/2003 | Harris et al. |
| 2003/0166371 A1 | 9/2003 | Fingal et al. |
| 2003/0176132 A1 | 9/2003 | Moriyasu et al. |
| 2003/0194558 A1 | 10/2003 | Anderson |
| 2003/0196955 A1 | 10/2003 | Hughes |
| 2004/0081829 A1 | 4/2004 | Klier et al. |
| 2004/0157037 A1 | 8/2004 | Yamaguchi et al. |
| 2004/0194558 A1 | 10/2004 | Nagase |
| 2004/0211729 A1 | 10/2004 | Sunkara et al. |
| 2004/0242838 A1 | 12/2004 | Duan |
| 2004/0258910 A1 | 12/2004 | Haile et al. |
| 2004/0260034 A1 | 12/2004 | Haile et al. |
| 2005/0026527 A1 | 2/2005 | Schmidt |
| 2005/0027098 A1 | 2/2005 | Hayes |
| 2005/0032450 A1 | 2/2005 | Haggard et al. |
| 2005/0079781 A1 | 4/2005 | Tsujimoto et al. |
| 2005/0115902 A1 | 6/2005 | Kaleem et al. |
| 2005/0125908 A1 | 6/2005 | Pourdeyhimi |
| 2005/0148261 A1 | 7/2005 | Close et al. |
| 2005/0171250 A1 | 8/2005 | Hayes |
| 2005/0208300 A1 | 9/2005 | Magill et al. |
| 2005/0221709 A1 | 10/2005 | Jordan et al. |
| 2005/0222956 A1 | 10/2005 | Bristow et al. |
| 2005/0227068 A1 | 10/2005 | Dugan |
| 2005/0282008 A1 | 12/2005 | Haile et al. |
| 2005/0287895 A1 | 12/2005 | Bansal |
| 2006/0011544 A1 | 1/2006 | Sharma et al. |
| 2006/0019570 A1 | 1/2006 | Groten et al. |
| 2006/0021938 A1 | 2/2006 | Diallo |
| 2006/0035556 A1 | 2/2006 | Yokoi et al. |
| 2006/0049386 A1 | 3/2006 | Kody et al. |
| 2006/0051575 A1 | 3/2006 | Yoon et al. |
| 2006/0057350 A1 | 3/2006 | Ochi et al. |
| 2006/0057373 A1 | 3/2006 | Inagaki et al. |
| 2006/0060529 A1 | 3/2006 | Cote et al. |
| 2006/0065600 A1 | 3/2006 | Sunkara et al. |
| 2006/0081330 A1 | 4/2006 | Minami et al. |
| 2006/0083917 A1 | 4/2006 | Dugan |
| 2006/0093814 A1 | 5/2006 | Chang |
| 2006/0093819 A1 | 5/2006 | Atwood et al. |
| 2006/0113033 A1 | 6/2006 | Bruner |
| 2006/0128247 A1 | 6/2006 | Skoog et al. |
| 2006/0135020 A1 | 6/2006 | Weinberg et al. |
| 2006/0147709 A1 | 7/2006 | Mizumura et al. |
| 2006/0159918 A1 | 7/2006 | Dugan et al. |
| 2006/0177656 A1 | 8/2006 | Kolmes et al. |
| 2006/0194047 A1 | 8/2006 | Gupta et al. |
| 2006/0204753 A1 | 9/2006 | Simmonds et al. |
| 2006/0210797 A1 | 9/2006 | Masuda et al. |
| 2006/0234049 A1 | 10/2006 | Van Dun et al. |
| 2006/0234050 A1 | 10/2006 | Frankel |
| 2006/0234587 A1 | 10/2006 | Horiguchi et al. |
| 2006/0263601 A1 | 11/2006 | Wang et al. |
| 2007/0009736 A1 | 1/2007 | Chuang et al. |
| 2007/0020453 A1 | 1/2007 | Sen et al. |
| 2007/0031637 A1 | 2/2007 | Anderson |
| 2007/0031668 A1 | 2/2007 | Hietpas et al. |
| 2007/0039889 A1 | 2/2007 | Ashford |
| 2007/0048523 A1 | 3/2007 | Pollet et al. |
| 2007/0056906 A1 | 3/2007 | Kaleem et al. |
| 2007/0062872 A1 | 3/2007 | Parker et al. |
| 2007/0074628 A1 | 4/2007 | Jones et al. |
| 2007/0098982 A1 | 5/2007 | Nishida et al. |
| 2007/0102361 A1 | 5/2007 | Kiefer et al. |
| 2007/0110980 A1 | 5/2007 | Shah |
| 2007/0110998 A1 | 5/2007 | Steele et al. |
| 2007/0114177 A1 | 5/2007 | Sabottke |
| 2007/0122613 A1 | 5/2007 | Stevens et al. |
| 2007/0122614 A1 | 5/2007 | Peng et al. |
| 2007/0128404 A1 | 6/2007 | Tung et al. |
| 2007/0179275 A1 | 8/2007 | Gupta et al. |
| 2007/0182040 A1 | 8/2007 | Suzuki et al. |
| 2007/0190319 A1 | 8/2007 | Kalayci |
| 2007/0232179 A1 | 10/2007 | Polat et al. |
| 2007/0232180 A1 | 10/2007 | Polat et al. |
| 2007/0243377 A1 | 10/2007 | Nishida et al. |
| 2007/0254153 A1 | 11/2007 | Nadkarni et al. |
| 2007/0258935 A1 | 11/2007 | McEntire et al. |
| 2007/0259029 A1 | 11/2007 | McEntire et al. |
| 2007/0259177 A1 | 11/2007 | Gupta et al. |
| 2007/0264520 A1 | 11/2007 | Wood et al. |
| 2007/0278151 A1 | 12/2007 | Musale |
| 2007/0278152 A1 | 12/2007 | Musale |
| 2008/0000836 A1 | 1/2008 | Wang et al. |
| 2008/0003905 A1 | 1/2008 | Tseng |
| 2008/0003912 A1 | 1/2008 | Pourdeyhimi et al. |
| 2008/0009574 A1 | 1/2008 | Huenefeld et al. |
| 2008/0009650 A1 | 1/2008 | Sluijmers et al. |
| 2008/0011680 A1 | 1/2008 | Partridge et al. |
| 2008/0038974 A1 | 2/2008 | Eagles |
| 2008/0039540 A1 | 2/2008 | Reitz |
| 2008/0064285 A1 | 3/2008 | Morton et al. |
| 2008/0134652 A1 | 6/2008 | Lim et al. |
| 2008/0160278 A1 | 7/2008 | Cheng et al. |
| 2008/0160859 A1 | 7/2008 | Gupta et al. |
| 2008/0170982 A1 | 7/2008 | Zhang et al. |
| 2008/0188151 A1 | 8/2008 | Yokoi et al. |
| 2008/0229672 A1 | 9/2008 | Woo et al. |
| 2008/0233850 A1 | 9/2008 | Woo et al. |
| 2008/0245037 A1 | 10/2008 | Rogers et al. |
| 2008/0287026 A1 | 11/2008 | Chakravarty et al. |
| 2008/0311815 A1 | 12/2008 | Gupta et al. |
| 2009/0025895 A1 | 1/2009 | Cowman |
| 2009/0036015 A1 | 2/2009 | Nhan et al. |
| 2009/0249956 A1 | 10/2009 | Chi et al. |
| 2009/0258182 A1 | 10/2009 | Okamoto et al. |
| 2009/0274862 A1 | 11/2009 | Nakayama et al. |
| 2009/0294435 A1 | 12/2009 | Nhan et al. |
| 2009/0305592 A1 | 12/2009 | Shi et al. |
| 2010/0018660 A1 | 1/2010 | Varnell |
| 2010/0035500 A1 | 2/2010 | Kimura et al. |
| 2010/0072126 A1 | 3/2010 | Tsujimoto et al. |
| 2010/0133173 A1 | 6/2010 | Inagaki |
| 2010/0136312 A1 | 6/2010 | Inagaki |
| 2010/0143717 A1 | 6/2010 | Sakamoto et al. |
| 2010/0173154 A1 | 7/2010 | Shimotsu |
| 2010/0180558 A1 | 7/2010 | Ito et al. |
| 2010/0203788 A1 | 8/2010 | Kimura et al. |
| 2010/0272938 A1 | 10/2010 | Mitchell et al. |
| 2010/0273947 A1 | 10/2010 | Miyauchi et al. |
| 2010/0282682 A1 | 11/2010 | Eaton et al. |
| 2010/0285101 A1 | 11/2010 | Moore et al. |
| 2010/0291213 A1 | 11/2010 | Berrigan et al. |
| 2010/0310921 A1 | 12/2010 | Hayakawa et al. |
| 2011/0020590 A1 | 1/2011 | Yoneda et al. |
| 2011/0030885 A1 | 2/2011 | Anneaux et al. |
| 2011/0033705 A1 | 2/2011 | Komura et al. |
| 2011/0036487 A1 | 2/2011 | Rajala et al. |
| 2011/0039055 A1 | 2/2011 | Fujisawa et al. |

| | | | | | | |
|---|---|---|---|---|---|---|
| 2011/0039468 | A1 | 2/2011 | Baldwin, Jr. et al. | JP | 1162825 A | 6/1989 |
| 2011/0040277 | A1 | 2/2011 | Rajala et al. | JP | 1-229899 A | 9/1989 |
| 2011/0041471 | A1 | 2/2011 | Sebastian et al. | JP | 1-272820 A | 10/1989 |
| 2011/0045042 | A1 | 2/2011 | Sasaki et al. | JP | 1-289838 A | 11/1989 |
| 2011/0045231 | A1 | 2/2011 | Kajiwara et al. | JP | 02-026920 A | 1/1990 |
| 2011/0045261 | A1 | 2/2011 | Sellars | JP | 2-210092 A | 8/1990 |
| 2011/0046461 | A1 | 2/2011 | McKenna | JP | 3-16378 B2 | 3/1991 |
| 2011/0049769 | A1 | 3/2011 | Duchoslav et al. | JP | 3-180587 A | 8/1991 |
| 2011/0054429 | A1 | 3/2011 | Lademann et al. | JP | 04-057918 A | 2/1992 |
| 2011/0059669 | A1 | 3/2011 | He et al. | JP | 04-327109 | 11/1992 |
| 2011/0064928 | A1 | 3/2011 | Bonneh | JP | 4327209 A | 11/1992 |
| 2011/0065573 | A1 | 3/2011 | McEneany et al. | JP | 5-18334 B2 | 3/1993 |
| 2011/0065871 | A1 | 3/2011 | Nagano et al. | JP | 05-263316 | 10/1993 |
| 2011/0067369 | A1 | 3/2011 | Chung et al. | JP | 1993-263316 A | 10/1993 |
| 2011/0068507 | A1 | 3/2011 | Warren et al. | JP | 5321106 A | 12/1993 |
| 2011/0074060 | A1 | 3/2011 | Angadjivand et al. | JP | 6-002221 A | 1/1994 |
| 2011/0076250 | A1 | 3/2011 | Belenkaya et al. | JP | 6-25396 A | 2/1994 |
| 2011/0084028 | A1 | 4/2011 | Stanfel et al. | JP | 9-77963 A | 3/1997 |
| 2011/0091761 | A1 | 4/2011 | Miller et al. | JP | 9-100397 A | 4/1997 |
| 2011/0094515 | A1 | 4/2011 | Duffy | JP | 9-249742 A | 9/1997 |
| 2011/0104493 | A1 | 5/2011 | Barnholtz et al. | JP | 09-291472 | 11/1997 |
| 2011/0114274 | A1 | 5/2011 | Takano et al. | JP | 09-310230 | 12/1997 |
| 2011/0117176 | A1 | 5/2011 | Klun et al. | JP | 2000-95850 | 4/2000 |
| 2011/0117353 | A1 | 5/2011 | Henshaw et al. | JP | 3131100 B2 | 1/2001 |
| 2011/0117439 | A1 | 5/2011 | Yamada et al. | JP | 2001-123335 | 5/2001 |
| 2011/0123584 | A1 | 5/2011 | Seidling et al. | JP | 2003-253555 A | 9/2003 |
| 2011/0124769 | A1 | 5/2011 | Moen et al. | JP | 2004-137319 | 5/2004 |
| 2011/0124835 | A1 | 5/2011 | DeWeijer et al. | JP | 2005-002510 | 1/2005 |
| 2011/0129510 | A1 | 6/2011 | Liebmann et al. | JP | 2005-154450 A | 6/2005 |
| 2011/0130063 | A1 | 6/2011 | Matsubayashi et al. | KR | 2011-031744 A | 3/2001 |
| 2011/0142900 | A1 | 6/2011 | Ohta et al. | KR | 2001-0044145 | 6/2001 |
| 2011/0143110 | A1 | 6/2011 | Tsuchiya et al. | KR | 531939 B1 | 11/2005 |
| 2011/0147299 | A1 | 6/2011 | Stanfel et al. | KR | 2011-031746 A | 3/2011 |
| 2011/0171535 | A1 | 7/2011 | Ohinshi et al. | RU | 2414950 C1 | 3/2011 |
| 2011/0171890 | A1 | 7/2011 | Nakayama et al. | RU | 2414960 C1 | 3/2011 |
| | | | | TW | 230212 B | 4/2005 |

FOREIGN PATENT DOCUMENTS

| | | | | | |
|---|---|---|---|---|---|
| EP | 1 416 077 A2 | 5/2004 | WO | WO 93/07197 A1 | 4/1993 |
| EP | 0 905 292 B1 | 10/2004 | WO | WO 94/24218 A | 10/1994 |
| EP | 1538686 A1 | 6/2005 | WO | WO 95/03172 A | 2/1995 |
| EP | 1 550 746 A1 | 7/2005 | WO | WO 99/47621 A1 | 9/1999 |
| EP | 1 322 802 B1 | 8/2005 | WO | WO 99/48668 | 9/1999 |
| EP | 1 314 808 B1 | 1/2006 | WO | WO 01/66666 A2 | 9/2001 |
| EP | 1252219 B1 | 8/2006 | WO | WO 02/060497 A2 | 8/2002 |
| EP | 1 325 184 B1 | 9/2006 | WO | WO 03/069038 A1 | 8/2003 |
| EP | 1 715 089 A2 | 10/2006 | WO | WO 2004/067818 A2 | 8/2004 |
| EP | 1 319 095 B1 | 11/2006 | WO | WO 2004/099314 A1 | 11/2004 |
| EP | 1 731 634 A | 12/2006 | WO | WO 2004/113598 A2 | 12/2004 |
| EP | 1 149 195 B1 | 1/2007 | WO | WO 2005/066403 A1 | 7/2005 |
| EP | 1 412 567 B1 | 1/2007 | WO | WO 2005/103354 A1 | 11/2005 |
| EP | 1 404 905 B1 | 4/2007 | WO | WO 2005/103357 A1 | 11/2005 |
| EP | 0 842 310 B1 | 1/2008 | WO | WO 2006/001739 A1 | 1/2006 |
| EP | 1 894 609 A1 | 3/2008 | WO | WO 2006/052732 A2 | 5/2006 |
| EP | 1 903 134 A1 | 3/2008 | WO | WO 2006/098851 A2 | 9/2006 |
| EP | 1 938 883 A1 | 7/2008 | WO | WO 2006/107695 A2 | 10/2006 |
| EP | 1 516 079 B1 | 12/2009 | WO | WO 2007/089423 A2 | 8/2007 |
| EP | 2 135 984 A1 | 12/2009 | WO | WO 2007/112443 A2 | 10/2007 |
| EP | 1 224 900 B1 | 6/2010 | WO | WO 2008/028134 A1 | 3/2008 |
| EP | 2 243 872 A1 | 10/2010 | WO | WO 2008/085332 A2 | 7/2008 |
| EP | 2283796 A1 | 2/2011 | WO | WO 2009/024836 A1 | 2/2009 |
| EP | 2287374 A1 | 2/2011 | WO | WO 2009/051283 A1 | 4/2009 |
| EP | 1 620 506 B1 | 3/2011 | WO | WO 2009/076401 A1 | 6/2009 |
| EP | 0847263 B2 | 3/2011 | WO | WO 2009/088564 A1 | 7/2009 |
| EP | 2292309 A1 | 3/2011 | WO | WO 2009/140381 A1 | 11/2009 |
| EP | 1474555 B1 | 4/2011 | WO | WO 2009/152349 A1 | 12/2009 |
| EP | 2308579 A1 | 4/2011 | WO | WO 2010/114820 A2 | 10/2010 |
| EP | 2311542 A1 | 4/2011 | WO | WO 2010/117612 A2 | 10/2010 |
| EP | 2311543 A1 | 4/2011 | WO | WO 2010/125239 A1 | 11/2010 |
| FR | 2654674 A1 | 5/1991 | WO | WO 2010/140853 A2 | 12/2010 |
| GB | 1073640 | 6/1967 | WO | WO 2010/146240 A2 | 12/2010 |
| JP | 52-066719 | 6/1977 | WO | WO 2011/015709 A1 | 2/2011 |
| JP | 58-83046 A | 5/1983 | WO | WO 2011/018459 A1 | 2/2011 |
| JP | 58174625 A | 10/1983 | WO | WO 2011/008481 A3 | 3/2011 |
| JP | 58-220818 | 12/1983 | WO | WO 2011/027732 A1 | 3/2011 |
| JP | 61-047822 | 3/1986 | WO | WO 2011/028661 A2 | 3/2011 |
| JP | 61-296120 A | 12/1986 | WO | WO 2011/034523 A1 | 3/2011 |
| JP | 62-078213 | 4/1987 | WO | WO 2011/047966 A1 | 4/2011 |
| JP | 63-159523 A | 7/1988 | WO | WO 2011/049831 A2 | 4/2011 |
| JP | S63-227898 A | 9/1988 | WO | WO 2011/049927 A2 | 4/2011 |
| | | | WO | WO 2011/052173 A1 | 5/2011 |

| | | | |
|---|---|---|---|
| WO | WO 2011/054932 A1 | 5/2011 |
| WO | WO 2011/062761 A1 | 5/2011 |
| WO | WO 2011/063372 A2 | 5/2011 |
| WO | WO 2011/066224 A2 | 6/2011 |
| WO | WO 2011/070233 A1 | 6/2011 |
| WO | 2011104427 A1 | 9/2011 |
| WO | 2011/157892 A1 | 12/2011 |

OTHER PUBLICATIONS

Manas-Zloczower and Tadmor, "Mixing and Compounding of Polymers," 1994, Carl Hanser Verlag Publisher, N.Y.
Office Action with Mail Date of Jan. 25, 2008 for related U.S. Appl. No. 11/343,955.
PCT International Search Report dated Feb. 4, 2008 for International Application No. PCT/US2007/001082.
U.S. Appl. No. 11/204,868, filed Aug. 16, 2005, William Alston Haile, et al.; now published as U.S. 2005-0282008 referenced above.
U.S. Appl. No. 11/343,955, filed Jan. 31, 2006, Rakesh Kumar Gupta, et al.; now published as 2007-0179275 referenced above.
U.S. Appl. No. 11/344,320, filed Jan. 31, 2006, Rakesh Kumar Gupta, et al.; now published as U.S. 2006-0194047 referenced above.
U.S. Appl. No. 11/648,953, filed Jan. 3, 2007, Rakesh Kumar Gupta, et al.; now published as U.S. 2008-0160859 referenced above.
U.S. Appl. No. 08/550,042, filed Oct. 30, 1995, Michael C. Cook.
Office Action with Mail Date of Oct. 10, 2008 for related U.S. Appl. No. 11/343,955.
PCT International Search Report dated Nov. 6, 2008 for International Application No. PCT/US2007/025661.
PCT International Search Report dated Jul. 26, 2007 for International Application No. PCT/US2007/001083.
Office Action with Mail Date of Mar. 30, 2009 for related U.S. Appl. No. 11/204,868.
Office Action with Mail Date of Mar. 26, 2009 for related U.S. Appl. No. 11/344,320.
Notice of Allowance; Date Mailed Mar. 9, 2009; for U.S. Appl. No. 11/343,955.
U.S. Appl. No. 61/172,257, filed Apr. 24, 2009, Rakesh Kumar Gupta, et al.
Lyondall Filtration and Separation; "Nonwoven Liquid Filtration Media Construction and Performance"; Accessed from the web: http://www.lydallfiltation.com/tech/documents/Nonwovenliquidfiltration.pdf.
PCT International Search Report dated Jul. 3, 2009 for International Application No. PCT/US2009/001717.
USPTO Notice of Allowance dated Nov. 9, 2009 for copending U.S. Appl. No. 11/648,955.
USPTO Office Action dated Dec. 24, 2009 for copending U.S. Appl. No. 11/344,320.
USPTO Office Action dated Dec. 22, 2009 for copending U.S. Appl. No. 11/204,868.
USPTO Notice of Allowance dated Jun. 9, 2010 for copending U.S. Appl. No. 11/344,320.
USPTO Notice of Allowance dated Jun. 9, 2010 for copending U.S. Appl. No. 11/204,868.
USPTO Office Action dated Aug. 6, 2010 for copending U.S. Appl. No. 11/648,953.
USPTO Office Action dated Dec. 21, 2004 for U.S. Appl. No. 10/850,548.
USPTO Notice of Allowance dated Jun. 8, 2005 for U.S. Appl. No. 10/850,548.
DIN STD 54900.
ASTM D6340-98.
PCT International Search Report dated Feb. 7, 2005 for International Application No. PCT/US2004/018682.
Copending U.S. Appl. No. 12/765,461, filed Apr. 22, 2010, Rakesh Kumar Gupta, et al.
Smook, G.A., "Handbook for Pulp and Paper Technologist", Angus Wilde Publications, $2^{nd}$ Ed., 1992, pp. 194-195, 211-212.
USPTO Notice of Allowance dated Aug. 7, 2009 for U.S. Appl. No. 11/343,955.
PCT International Search Report dated Dec. 30, 2009 for International Application No. PCT/US2007/025770.
Ke Qinfei, et al., "Non-woven Science", Donghau University Press, 2004.9, Catalog, p. 115-132 (unavailable).
USPTO Office Action dated Jan. 25, 2008 for U.S. Appl. No. 11/343,955.
USPTO Notice of Allowance dated Nov. 9, 2009 for U.S. Appl. No. 11/648,955.
USPTO Office Action dated Sep. 27, 2010 for U.S. Appl. No. 12/199,304.
USPTO Notice of Allowance dated Sep. 30, 2010 for U.S. Appl. No. 11/344,320.
USPTO Notice of Allowance dated Oct. 14, 2010 for U.S. Appl. No. 11/204,868.
Copending U.S. Appl. No. 12/909,574, filed Oct. 21, 2010, Rakesh Kumar Gupta, et al.
Copending U.S. Appl. No. 12/966,483, filed Dec. 13, 2010, William Alston Haile, et al.
Copending U.S. Appl. No. 12/966,487, filed Dec. 13, 2010, William Alston Haile, et al.
Copending U.S. Appl. No. 12/966,494, filed Dec. 13, 2010, William Alston Haile, et al.
Copending U.S. Appl. No. 12/966,507, filed Dec. 13, 2010, William Alston Haile, et al.
Copending U.S. Appl. No. 12/966,512, filed Dec. 13, 2010, William Alston Haile, et al.
Copending U.S. Appl. No. 12/966,518, filed Dec. 13, 2010, William Alston Haile, et al.
Copending U.S. Appl. No. 12/966,521, filed Dec. 13, 2010, William Alston Haile, et al.
Copending U.S. Appl. No. 12/975,443, filed Dec. 22, 2010, Rakesh Kumar Gupta, et al.
Copending U.S. Appl. No. 12/975,447, filed Dec. 22, 2010, Rakesh Kumar Gupta, et al.
Copending U.S. Appl. No. 12/975,450, filed Dec. 22, 2010, Rakesh Kumar Gupta, et al.
Copending U.S. Appl. No. 12/975,452, filed Dec. 22, 2010, Rakesh Kumar Gupta, et al.
Copending U.S. Appl. No. 12/975,456, filed Dec. 22, 2010, Rakesh Kumar Gupta, et al.
Copending U.S. Appl. No. 12/975,459, filed Dec. 22, 2010, Rakesh Kumar Gupta, et al.
Copending U.S. Appl. No. 12/975,463, filed Dec. 22, 2010, Rakesh Kumar Gupta, et al.
Copending U.S. Appl. No. 12/975,482, filed Dec. 22, 2010, Rakesh Kumar Gupta, et al.
Copending U.S. Appl. No. 12/975,484, filed Dec. 22, 2010, Rakesh Kumar Gupta, et al.
Copending U.S. Appl. No. 12/975,487, filed Dec. 22, 2010, Rakesh Kumar Gupta, et al.
Copending U.S. Appl. No. 12/981,950, filed Dec. 30, 2010, William Alston Haile, et al.
Copending U.S. Appl. No. 12/981,960, filed Dec. 30, 2010, William Alston Haile, et al.
Copending U.S. Appl. No. 12/981,982, filed Dec. 30, 2010, William Alston Haile, et al.
Copending U.S. Appl. No. 12/982,001, filed Dec. 30, 2010, William Alston Haile, et al.
Coons, R., "Eastman Chemical Core Focus Delivers Value," Chemical Week, Aug. 15/22, 2011, pp. 19-22.
USPTO Office Action dated Sep. 15, 2011 for copending U.S. Appl. No. 11/648,953.
USPTO Office Action dated Sep. 8, 2011 for copending U.S. Appl. No. 12/966,494.
USPTO Office Action dated Sep. 26, 2011 for copending U.S. Appl. No. 12/966,507.
USPTO Office Action dated Sep. 1, 2011 for copending U.S. Appl. No. 12/975,450.
USPTO Office Action dated Aug. 24, 2011 for copending U.S. Appl. No. 12/975,456.
USPTO Office Action dated Sep. 27, 2011 for copending U.S. Appl. No. 12/975,463.
USPTO Office Action dated Aug. 31, 2011 for copending U.S. Appl. No. 13/053,615.

New copending U.S. Appl. No. 13/053,615, filed on Mar. 22, 2011, Rakesh Kumar Gupta et al.
USPTO Notice of Allowance dated Apr. 4, 2011 for copending U.S. Appl. No. 12/199,304.
USPTO Office Action dated Mar. 18, 2011 for copending U.S. Appl. No. 11/648,953.
USPTO Office Action dated Apr. 6, 2011 for copending U.S. Appl. No 12/975,487.
USPTO Office Action dated Apr. 4, 2011 for copending U.S. Appl. No. 12/981,960.
USPTO Office Action dated Apr. 6, 2011 for copending U.S. Appl. No. 12/975,482.
USPTO Office Action dated Jun. 7, 2011 for copending U.S. Appl. No. 12/982,001.
USPTO Office Action dated Jun. 9, 2011 for copending U.S. Appl. No. 12/975,459.
USPTO Office Action dated May 27, 2011 for copending U.S. Appl. No. 12/975,452.
USPTO Office Action dated Jun. 23, 2011 for copending U.S. Appl. No. 12/966,487.
USPTO Office Action dated Jun. 23, 2011 for copending U.S. Appl. No. 12/966,502.
USPTO Office Action dated Jun 23, 2011 for copending U.S. Appl. No. 12/975,443.
USPTO Notice of Allowance dated Jul. 18, 2011 for copending U.S. Appl. No. 12/199,304.
USPTO Office Action dated Aug. 10, 2011 for copending U.S. Appl. No. 12/966,512.
New copending U.S. Appl. No. 13/352,362, filed on Jan. 18, 2012, Rakesh Kumar Gupta et al.
USPTO Office Action dated Nov. 10, 2011 for copending U.S. Appl. No. 12/981,950.
USPTO Office Action dated Jan. 25, 2012 for copending U.S. Appl. No. 12/981,982.
USPTO Notice of Allowance dated Jan. 3, 2012 for copending U.S. Appl. No. 12/975,487.
USPTO Notice of Allowance dated Dec. 23, 2011 for copending U.S. Appl. No. 12/975,452.
USPTO Notice of Allowance dated Dec. 8, 2011 for copending U.S. Appl. No. 12/981,960.
USPTO Notice of Allowance dated Dec. 13, 2011 for copending U.S. Appl. No. 12/966,487.
USPTO Notice of Allowance dated Dec. 12, 2011 for copending U.S. Appl. No. 12/966,502.
USPTO Notice of Allowance dated Dec. 9, 2011 for copending U.S. Appl. No. 12/966,512.
USPTO Notice of Allowance dated Jan. 9, 2012 for copending U.S. Appl. No. 12/975,482.
USPTO Office Action dated Jan. 30, 2012 for copending U.S. Appl. No. 12/975,443.
USPTO Office Action dated Nov. 10, 2011 for copending U.S. Appl. No. 12/975,484.
New copending U.S. Appl. No. 13/273,692, filed on Oct. 14, 2011, Rakesh Kumar Gupta, et al.
New copending U.S. Appl. No. 13/273,648, filed on Oct. 14, 2011, Rakesh Kumar Gupta, et al.
New copending U.S. Appl. No. 13/273,710, filed on Oct. 14, 2011, Rakesh Kumar Gupta, et al.
New copending U.S. Appl. No. 13/273,720, filed on Oct. 14, 2011, Rakesh Kumar Gupta, et al.
New copending U.S. Appl. No. 13/273,929, filed on Oct. 14, 2011, Rakesh Kumar Gupta, et al.
New copending U.S. Appl. No. 13/273,937, filed on Oct. 14, 2011, Rakesh Kumar Gupta, et al.
New copending U.S. Appl. No. 13/273,727, filed on Oct. 14, 2011, Rakesh Kumar Gupta, et al.
New copending U.S. Appl. No. 13/273,737, filed on Oct. 14, 2011, Rakesh Kumar Gupta, et al.
New copending U.S. Appl. No. 13/273,745, filed on Oct. 14, 2011, Rakesh Kumar Gupta, et al.
New copending U.S. Appl. No. 13/273,749, filed on Oct. 14, 2011, Rakesh Kumar Gupta, et al.
USPTO Notice of Allowance dated Feb. 7, 2012 for copending U.S. Appl. No. 12/975,459.
USPTO Notice of Allowance dated Feb. 17, 2012 for copending U.S. Appl. No. 12/982,001.
USPTO Notice of Allowance dated Feb. 23, 2012 for copending U.S. Appl. No. 13/053,615.
Office Action with Mail Date of Mar. 2, 2012 for copending U.S. Appl. No. 12/966,518.
Office Action with Mail Date of Nov. 10, 2011 for copending U.S. Appl. No. 12/975,447.
USPTO Notice of Allowance dated Feb. 21, 2012 for copending U.S. Appl. No. 12/975,450.
Office Action with Mail Date of Jan. 30, 2012 for copending U.S. Appl. No. 12/978,443.
U.S. Appl. No. 11/648,955, filed Jan. 3, 2007, Rakesh Kumar Gupta, et al.
PCT International Search Report dated Feb. 4, 2008 for International Application No. PCT/US2007/025770.
Database WPI, Week 200450, Thomson Scientific, London, GB; AN 2004/520211 XP002639794 & JP 2004/137418A May 13, 2004—abstract—.
USPTO Notice of Allowance dated Apr. 13, 2012 for copending U.S. Appl. No. 12/966,487.
USPTO Office Action dated Apr. 19, 2012 for copending U.S. Appl. No. 12/975,456.
USPTO Notice of Allowance dated Apr. 18, 2012 for copending U.S. Appl. No. 12/966,494.
USPTO Notice of Allowance dated Apr. 18, 2012 for copending U.S. Appl. No. 12/975,484.
USPTO Office Action dated Apr. 19, 2012 for copending U.S. Appl. No. 12/975,463.
USPTO Office Action dated Mar. 16, 2012 for copending U.S. Appl. No. 12/966,483.
USPTO Notice of Allowance dated Apr. 2, 2012 for copending U.S. Appl. No. 12/966,502.
USPTO Notice of Allowance dated Mar. 21, 2012 for copending U.S. Appl. No. 12/966,512.
USPTO Notice of Allowance dated Apr. 2, 2012 for copending U.S. Appl. No. 12/975,452.
USPTO Notice of Allowance dated Mar. 15, 2012 for copending U.S. Appl. No. 12/981,960.
USPTO Office Action dated May 10, 2012 for copending U.S. Appl. No. 12/966,521.
USPTO Office Action dated Apr. 23, 2012 for copending U.S. Appl. No. 12/966,507.
USPTO Office Action dated May 3, 2012 for copending U.S. Appl. No. 12/765,461.
USPTO Office Action dated May 21, 2011 for copending U.S. Appl. No. 12/981,982.

* cited by examiner

WATER-DISPERSIBLE AND MULTICOMPONENT FIBERS FROM SULFOPOLYESTERS

CROSS REFERENCES TO RELATED APPLICATIONS

This application is a continuation application claiming priority to application Ser. No. 11/204,868 filed on Aug. 16, 2005 now U.S. Pat. No. 7,902,094 which is a divisional of application Ser. No. 10/850,548, filed May 20, 2004, now issued as U.S. Pat. No. 6,989,193, which is a continuation-in-part of application Ser. No. 10/465,698, filed Jun. 19, 2003, now abandoned; all of which are hereby incorporated by reference to the extent they do contradict the statements herein.

FIELD OF THE INVENTION

The present invention pertains to water-dispersible fibers and fibrous articles comprising a sulfopolyester. The invention further pertains to multicomponent fibers comprising a sulfopolyester and the microdenier fibers and fibrous articles prepared therefrom. The invention also pertains to processes for water-dispersible, multicomponent, and microdenier fibers and to nonwoven fabrics prepared therefrom. The fibers and fibrous articles have applications in flushable personal care products and medical products.

BACKGROUND OF THE INVENTION

Fibers, melt blown webs and other melt spun fibrous articles have been made from thermoplastic polymers, such as poly(propylene), polyamides, and polyesters. One common application of these fibers and fibrous articles are nonwoven fabrics and, in particular, in personal care products such as wipes, feminine hygiene products, baby diapers, adult incontinence briefs, hospital/surgical and other medical disposables, protective fabrics and layers, geotextiles, industrial wipes, and filter media. Unfortunately, the personal care products made from conventional thermoplastic polymers are difficult to dispose of and are usually placed in landfills. One promising alternative method of disposal is to make these products or their components "flushable", i.e., compatible with public sewerage systems. The use of water-dispersible or water-soluble materials also improves recyclability and reclamation of personal care products. The various thermoplastic polymers now used in personal care products are not inherently water-dispersible or soluble and, hence, do not produce articles that readily disintegrate and can be disposed of in a sewerage system or recycled easily.

The desirability of flushable personal care products has resulted in a need for fibers, nonwovens, and other fibrous articles with various degrees of water-responsivity. Various approaches to addressing these needs have been described, for example, in U.S. Pat. Nos. 6,548,592; 6,552,162; 5,281, 306; 5,292,581; 5,935,880; and 5,509,913; U.S. patent application Ser. Nos. 09/775,312; and 09/752,017; and PCT International Publication No. WO 01/66666 A2. These approaches, however, suffer from a number of disadvantages and do not provide a fibrous article, such as a fiber or nonwoven fabric, that possesses a satisfactory balance of performance properties, such as tensile strength, absorptivity, flexibility, and fabric integrity under both wet or dry conditions.

For example, typical nonwoven technology is based on the multidirectional deposition of fibers that are treated with a resin binding adhesive to form a web having strong integrity and other desirable properties. The resulting assemblies, however, generally have poor water-responsivity and are not suitable for flushable applications. The presence of binder also may result in undesirable properties in the final product, such as reduced sheet wettability, increased stiffness, stickiness, and higher production costs. It is also difficult to produce a binder that will exhibit adequate wet strength during use and yet disperse quickly upon disposal. Thus, nonwoven assemblies using these binders may either disintegrate slowly under ambient conditions or have less than adequate wet strength properties in the presence of body fluids. To address this problem, pH and ion-sensitive water-dispersible binders, such as lattices containing acrylic or methacrylic acid with or without added salts, are known and described, for example, in U.S. Pat. No. 6,548,592 B1. Ion concentrations and pH levels in public sewerage and residential septic systems, however, can vary widely among geographical locations and may not be sufficient for the binder to become soluble and disperse. In this case, the fibrous articles will not disintegrate after disposal and can clog drains or sewer laterals.

Multicomponent fibers containing a water-dispersible component and a thermoplastic water non-dispersible component have been described, for example, in U.S. Pat. Nos. 5,916,678; 5,405,698; 4,966,808; 5,525,282; 5,366,804; 5,486,418. For example, these multicomponent fibers may be a bicomponent fiber having a shaped or engineered transverse cross section such as, for example, an islands-in-the-sea, sheath core, side-by-side, or segmented pie configuration. The multicomponent fiber can be subjected to water or a dilute alkaline solution where the water-dispersible component is dissolved away to leave the water non-dispersible component behind as separate, independent fibers of extremely small fineness. Polymers which have good water dispersibility, however, often impart tackiness to the resulting multicomponent fibers, which causes the fiber to stick together, block, or fuse during winding or storage after several days, especially under hot, humid conditions. To prevent fusing, often a fatty acid or oil-based finish is applied to the surface of the fiber. In addition, large proportions of pigments or fillers are sometimes added to water dispersible polymers to prevent fusing of the fibers as described, for example, in U.S. Pat. No. 6,171,685. Such oil finishes, pigments, and fillers require additional processing steps and can impart undesirable properties to the final fiber. Many water-dispersible polymers also require alkaline solutions for their removal which can cause degradation of the other polymer components of the fiber such as, for example, reduction of inherent viscosity, tenacity, and melt strength. Further, some water-dispersible polymers can not withstand exposure to water during hydroentanglement and, thus, are not suitable for the manufacture of nonwoven webs and fabrics.

Alternatively, the water-dispersible component may serve as a bonding agent for the thermoplastic fibers in nonwoven webs. Upon exposure to water, the fiber to fiber bonds come apart such that the nonwoven web loses its integrity and breaks down into individual fibers. The thermoplastic fiber components of these nonwoven webs, however, are not water-dispersible and remain present in the aqueous medium and, thus, must eventually be removed from municipal wastewater treatment plants. Hydroentanglement may be used to produce disintegratable nonwoven fabrics without or with very low levels (<5 wt %) of added binder to hold the fibers together. Although these fabrics may disintegrate upon disposal, they often utilize fibers that are not water soluble or water-dispersible and may result in entanglement and plugging within sewer systems. Any added water-dispersible binders also must be minimally affected by hydroentangling and not form gelatinous buildup or cross-link, and thereby contribute to fabric handling or sewer related problems.

A few water-soluble or water-dispersible polymers are available, but are generally not applicable to melt blown fiber forming operations or melt spinning in general. Polymers, such as polyvinyl alcohol, polyvinyl pyrrolidone, and polyacrylic acid are not melt processable as a result of thermal decomposition that occurs at temperatures below the point where a suitable melt viscosity is attained. High molecular weight polyethylene oxide may have suitable thermal stability, but would provide a high viscosity solution at the polymer interface resulting in a slow rate of disintegration. Water-dispersible sulfopolyesters have been described, for example, in U.S. Pat. Nos. 6,171,685; 5,543,488; 5,853,701; 4,304,901; 6,211,309; 5,570,605; 6,428,900; and 3,779,993. Typical sulfopolyesters, however, are low molecular weight thermoplastics that are brittle and lack the flexibility to withstand a winding operation to yield a roll of material that does not fracture or crumble. Sulfopolyesters also can exhibit blocking or fusing during processing into film or fibers, which may require the use of oil finishes or large amounts of pigments or fillers to avoid. Low molecular weight polyethylene oxide (more commonly known as polyethylene glycol) is a weak/brittle polymer that also does not have the required physical properties for fiber applications. Forming fibers from known water-soluble polymers via solution techniques is an alternative, but the added complexity of removing solvent, especially water, increases manufacturing costs.

Accordingly, there is a need for a water-dispersible fiber and fibrous articles prepared therefrom that exhibit adequate tensile strength, absorptivity, flexibility, and fabric integrity in the presence of moisture, especially upon exposure to human bodily fluids. In addition, a fibrous article is needed that does not require a binder and completely disperses or dissolves in residential or municipal sewerage systems. Potential uses include, but are not limited to, melt blown webs, spunbond fabrics, hydroentangled fabrics, dry-laid non-wovens, bicomponent fiber components, adhesive promoting layers, binders for cellulosics, flushable nonwovens and films, dissolvable binder fibers, protective layers, and carriers for active ingredients to be released or dissolved in water. There is also a need for multicomponent fiber having a water-dispersible component that does not exhibit excessive blocking or fusing of filaments during spinning operations, is easily removed by hot water at neutral or slightly acidic pH, and is suitable for hydroentangling processes to manufacture nonwoven fabrics. Other extrudable and melt spun fibrous materials are also possible.

SUMMARY OF THE INVENTION

We have unexpectedly discovered that flexible, water-dispersible fibers may be prepared from sulfopolyesters. Thus the present invention provides a water-dispersible fiber comprising:
(A) a sulfopolyester having a glass transition temperature (Tg) of at least 25° C., the sulfopolyester comprising:
  (i) residues of one or more dicarboxylic acids;
  (ii) about 4 to about 40 mole %, based on the total repeating units, of residues of at least one sulfomonomer having 2 functional groups and one or more sulfonate groups attached to an aromatic or cycloaliphatic ring wherein the functional groups are hydroxyl, carboxyl, or a combination thereof;
  (iii) one or more diol residues wherein at least 25 mole %, based on the total diol residues, is a poly(ethylene glycol) having a structure H—(OCH$_2$—CH$_2$)$_n$—OH wherein n is an integer in the range of 2 to about 500; and
  (iv) 0 to about 25 mole %, based on the total repeating units, of residues of a branching monomer having 3 or more functional groups wherein the functional groups are hydroxyl, carboxyl, or a combination thereof;
(B) optionally, a water-dispersible polymer blended with the sulfopolyester; and
(C) optionally, a water-nondispersible polymer blended with the sulfopolyester with the proviso that the blend is an immiscible blend;
wherein the fiber contains less than 10 weight percent of a pigment or filler, based on the total weight of the fiber.

The fibers of the present invention may be unicomponent fibers that rapidly disperse or dissolve in water and may be produced by melt-blowing or melt-spinning. The fibers may be prepared from a single sulfopolyester or a blend of the sulfopolyester with a water-dispersible or water-nondispersible polymer. Thus, the fiber of the present invention, optionally, may include a water-dispersible polymer blended with the sulfopolyester. In addition, the fiber may optionally include a water-nondispersible polymer blended with the sulfopolyester, provided that the blend is an immiscible blend. Our invention also includes fibrous articles comprising our water-dispersible fibers. Thus, the fibers of our invention may be used to prepare various fibrous articles, such as yarns, melt-blown webs, spunbonded webs, and nonwoven fabrics that are, in turn, water-dispersible or flushable. Staple fibers of our invention can also be blended with natural or synthetic fibers in paper, nonwoven webs, and textile yarns.

Another aspect of the present invention is a water-dispersible fiber comprising:
A) a sulfopolyester having a glass transition temperature (Tg) of at least 25° C., the sulfopolyester comprising:
  (i) about 50 to about 96 mole % of one or more residues of isophthalic acid or terephthalic acid, based on the total acid residues;
  (ii) about 4 to about 30 mole %, based on the total acid residues, of a residue of sodiosulfoisophthalic acid;
  (iii) one or more diol residues wherein at least 25 mole %, based on the total diol residues, is a poly(ethylene glycol) having a structure H—(OCH$_2$—CH$_2$)$_n$—OH wherein n is an integer in the range of 2 to about 500;
  (iv) 0 to about 20 mole %, based on the total repeating units, of residues of a branching monomer having 3 or more functional groups wherein the functional groups are hydroxyl, carboxyl, or a combination thereof;
(B) optionally, a first water-dispersible polymer blended with the sulfopolyester; and
(C) optionally, a water-nondispersible polymer blended with the sulfopolyester to form a blend with the proviso that the blend is an immiscible blend;
wherein the fiber contains less than 10 weight percent of a pigment or filler, based on the total weight of the fiber.

The water-dispersible, fibrous articles of the present invention include personal care articles such as, for example, wipes, gauze, tissue, diapers, training pants, sanitary napkins, bandages, wound care, and surgical dressings. In addition to being water-dispersible, the fibrous articles of our invention are flushable, that is, compatible with and suitable for disposal in residential and municipal sewerage systems.

The present invention also provides a multicomponent fiber comprising a water-dispersible sulfopolyester and one or more water non-dispersible polymers. The fiber has an engineered geometry such that the water non-dispersible polymers are present as segments substantially isolated from each other by the intervening sulfopolyester, which acts as a binder or encapsulating matrix for the water non-dispersible segments. Thus, another aspect of our invention is a multicomponent fiber having a shaped cross section, comprising:
A) a water dispersible sulfopolyester having a glass transition temperature (Tg) of at least 57° C., the sulfopolyester comprising:
   (i) residues of one or more dicarboxylic acids;
   (ii) about 4 to about 40 mole %, based on the total repeating units, of residues of at least one sulfomonomer having 2 functional groups and one or more sulfonate groups attached to an aromatic or cycloaliphatic ring wherein the functional groups are hydroxyl, carboxyl, or a combination thereof;
   (iii) one or more diol residues wherein at least 25 mole %, based on the total diol residues, is a poly(ethylene glycol) having a structure

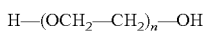

wherein n is an integer in the range of 2 to about 500; and
   (iv) 0 to about 25 mole %, based on the total repeating units, of residues of a branching monomer having 3 or more functional groups wherein the functional groups are hydroxyl, carboxyl, or a combination thereof; and
B) a plurality of segments comprising one or more water-nondispersible polymers immiscible with the sulfopolyester, wherein the segments are substantially isolated from each other by the sulfopolyester intervening between the segments;
wherein the fiber contains less than 10 weight percent of a pigment or filler, based on the total weight of the fiber.
The sulfopolyester has a glass transition temperature of at least 57° C. which greatly reduces blocking and fusion of the fiber during winding and long term storage. The sulfopolyester may be removed by contacting the multicomponent fiber with water to leave behind the water non-dispersible segments as microdenier fibers. Our invention, therefore, also provides a process for microdenier fibers comprising:
A. spinning a water dispersible sulfopolyester having a glass transition temperature (Tg) of at least 57° C. and one or more water-nondispersable polymers immiscible with the sulfopolyester into multicomponent fibers, the sulfopolyester comprising:
   (i) about 50 to about 96 mole % of one or more residues of isophthalic acid or terephthalic acid, based on the total acid residues;
   (ii) about 4 to about 30 mole %, based on the total acid residues, of a residue of sodiosulfoisophthalic acid;
   (iii) one or more diol residues wherein at least 25 mole %, based on the total diol residues, is a poly(ethylene glycol) having a structure

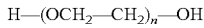

wherein n is an integer in the range of 2 to about 500; and
   (iv) 0 to about 20 mole %, based on the total repeating units, of residues of a branching monomer having 3 or more functional groups wherein the functional groups are hydroxyl, carboxyl, or a combination thereof;
wherein the fibers have a plurality of segments comprising the water-nondispersable polymers wherein the segments are substantially isolated from each other by the sulfopolyester intervening between the segments and the fibers contain less than 10 weight percent of a pigment or filler, based on the total weight of the fibers; and
B. contacting the multicomponent fibers with water to remove the sulfopolyester thereby forming microdenier fibers.

The water non-dispersible polymers may be biodistintegratable as determined by DIN Standard 54900 and/or biodegradable as determined by ASTM Standard Method, D6340-98. The multicomponent fiber also may be used to prepare a fibrous article such as a yarn, fabric, melt-blown web, spun-bonded web, or non-woven fabric and which may comprise one or more layers of fibers. The fibrous article having multicomponent fibers, in turn, may be contacted with water to produce fibrous articles containing microdenier fibers. Thus, another aspect of the invention is a process for a microdenier fiber web, comprising:
A. spinning a water dispersible sulfopolyester having a glass transition temperature (Tg) of at least 57° C. and one or more water-nondispersable polymers immiscible with the sulfopolyester into multicomponent fibers, the sulfopolyester comprising:
   (i) about 50 to about 96 mole % of one or more residues of isophthalic acid or terephthalic acid, based on the total acid residues;
   (ii) about 4 to about 30 mole %, based on the total acid residues, of a residue of sodiosulfoisophthalic acid;
   (iii) one or more diol residues wherein at least 25 mole %, based on the total diol residues, is a poly(ethylene glycol) having a structure

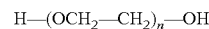

wherein n is an integer in the range of 2 to about 500; and
   (iv) 0 to about 20 mole %, based on the total repeating units, of residues of a branching monomer having 3 or more functional groups wherein the functional groups are hydroxyl, carboxyl, or a combination thereof.
wherein the multicomponent fibers have a plurality of segments comprising the water-nondispersible polymers and the segments are substantially isolated from each other by the sulfopolyester intervening between the segments and the fibers contain less than 10 weight percent of a pigment or filler, based on the total weight of said fibers;
B. overlapping and collecting the multicomponent fibers of Step A to form a nonwoven web; and
C. contacting the nonwoven web with water to remove the sulfopolyester thereby forming a microdenier fiber web.

Our invention also provides a process for a process for water-dispersible, nonwoven fabric comprising:
I. heating a water-dispersible polymer composition to a temperature above its flow point, wherein the polymer composition comprises
   (A) a sulfopolyester having a glass transition temperature (Tg) of at least 25° C., the sulfopolyester comprising:
      (i) residues of one or more dicarboxylic acids;
      (ii) about 4 to about 40 mole %, based on the total repeating units, of residues of at least one sulfomonomer having 2 functional groups and one or more metal sulfonate groups attached to an aromatic or cycloaliphatic ring wherein the functional groups are hydroxyl, carboxyl, or a combination thereof;
      (iii) one or more diol residues wherein at least 20 mole %, based on the total diol residues, is a poly(ethylene glycol) having a structure

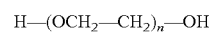

wherein n is an integer in the range of 2 to about 500;
      (iv) 0 to about 25 mole %, based on the total repeating units, of residues of a branching monomer having 3 or more functional groups wherein the functional groups are hydroxyl, carboxyl, or a combination thereof;

(B) optionally, a water-dispersible polymer blended with the sulfopolyester; and (C) optionally, a water-nondispersible polymer blended with the sulfopolyester to form a blend with the proviso that the blend is an immiscible blend;

wherein the polymer composition contains less than 10 weight percent of a pigment or filler, based on the total weight of the polymer composition;

II. melt spinning filaments; and

III. overlapping and collecting the filaments of Step II to form a nonwoven web.

Our invention thus offers a novel and inexpensive process for a water-dispersible nonwoven fabric by melt-spinning a water-dispersible sulfopolyester and forming a nonwoven web. The nonwoven fabric may be in the form of a flat fabric or a 3-dimensional shape and may be incorporated into a variety of fibrous articles such as the personal care articles noted hereinabove or used for the manufacture of water-dispersible and/or flushable protective outerware such as, for example, surgical gowns and protective clothing for chemical and biohazard cleanup and laboratory work.

DETAILED DESCRIPTION

The present invention provides water-dispersible fibers and fibrous articles that show tensile strength, absorptivity, flexibility, and fabric integrity in the presence of moisture, especially upon exposure to human bodily fluids. The fibers and fibrous articles of our invention do not require the presence of oil, wax, or fatty acid finishes or the use of large amounts (typically 10 wt % or greater) of pigments or fillers to prevent blocking or fusing of the fibers during processing. In addition, the fibrous articles prepared from our novel fibers do not require a binder and readily disperse or dissolve in home or public sewerage systems. In a general embodiment, our invention provides a water-dispersible fiber comprising a sulfopolyester having a glass transition temperature (Tg) of at least 25° C., wherein the sulfpolyester comprises: (i) residues of one or more dicarboxylic acids; (ii) about 4 to about 40 mole %, based on the total repeating units, of residues of at least one sulfomonomer having 2 functional groups and one or more sulfonate groups attached to an aromatic or cycloaliphatic ring wherein the functional groups are hydroxyl, carboxyl, or a combination thereof; (iii) one or more diol residues wherein at least 25 mole %, based on the total diol residues, is a poly(ethylene glycol) having a structure

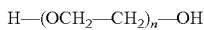

wherein n is an integer in the range of 2 to about 500; and (iv) 0 to about 25 mole %, based on the total repeating units, of residues of a branching monomer having 3 or more functional groups wherein the functional groups are hydroxyl, carboxyl, or a combination thereof. Our fiber may optionally include a water-dispersible polymer blended with the sulfopolyester and, optionally, a water-nondispersible polymer blended with the sulfopolyester with the proviso that the blend is an immiscible blend. Our fiber contains less than 10 weight percent of a pigment or filler, based on the total weight of the fiber. The present invention also includes fibrous articles comprising these fibers and may include personal care products such as wipes, gauze, tissue, diapers, adult incontinence briefs, training pants, sanitary napkins, bandages, and surgical dressings. The fibrous articles may have one or more absorbent layers of fibers.

The fibers of our invention may be unicomponent fibers, bicomponent or multicomponent fibers. For example, the fibers of the present invention may be prepared by melt spinning a single sulfopolyester or sulfopolyester blend and include staple, monofilament, and multifilament fibers with a shaped cross-section. In addition, our invention provides multicomponent fibers, such as described, for example, in U.S. Pat. No. 5,916,678, which may be prepared by extruding the sulfopolyester and one or more water non-dispersible polymers, which are immiscible with the sulfopolyester, separately through a spinneret having a shaped or engineered transverse geometry such as, for example, an "islands-in-the-sea", sheath-core, side-by-side, or segmented pie configuration. The sulfopolyester may be later removed by dissolving the interfacial layers or pie segments and leaving the smaller filaments or microdenier fibers of the water non-dispersible polymer(s). For example, the sulfopolyester and water non-dispersible polymers may be fed to a polymer distribution system where the polymers are introduced into a segmented spinneret plate. The polymers follow separate paths to the fiber spinneret and are combined at the spinneret hole which comprises either two concentric circular holes thus providing a sheath-core type fiber, or a circular spinneret hole divided along a diameter into multiple parts to provide a fiber having a side-by-side type. Alternatively, the immiscible water dispersible sulfopolyester and water non-dispersible polymers may be introduced separately into a spinneret having a plurality of radial channels to produce a multicomponent fiber having a segmented pie cross section. Typically, the sulfopolyester will form the "sheath" component of a sheath core configuration. In fiber cross sections having a plurality of segments, the water non-dispersible segments, typically, are substantially isolated from each other by the sulfopolyester. Alternatively, multicomponent fibers may be formed by melting the sulfopolyester and water non-dispersible polymers in separate extruders and directing the polymer flows into one spinneret with a plurality of distribution flow paths in form of small thin tubes or segments to provide a fiber having an islands-in-the-sea shaped cross section. An example of such a spinneret is described in U.S. Pat. No. 5,366,804. In the present invention, typically, the sulfopolyester will form the "sea" component and the water non-dispersible polymer will for the "islands" component.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "C1 to C5 hydrocarbons", is intended to specifically include and disclose C1 and C5 hydrocarbons as well as C2, C3, and C4 hydrocarbons.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

The unicomponent fibers and fibrous articles of the present invention are water-dispersible and, typically, completely disperse at room temperature. Higher water temperatures can be used to accelerate their dispersibility or rate of removal from the nonwoven or multicomponent fiber. The term "water-dispersible", as used herein with respect to unicomponent fibers and fibrous articles prepared from unicomponent fibers, is intended to be synonymous with the terms "water-dissipatable", "water-disintegratable", "water-dissolvable", "water-dispellable", "water soluble", water-removable", "hydrosoluble", and "hydrodispersible" and is intended to mean that the fiber or fibrous article is therein or therethrough dispersed or dissolved by the action of water. The terms "dispersed", "dispersible", "dissipate", or "dissipatable" mean that, using a sufficient amount of deionized water (e.g., 100:1 water:fiber by weight) to form a loose suspension or slurry of the fibers or fibrous article, at a temperature of about 60° C., and within a time period of up to 5 days, the fiber or fibrous article dissolves, disintegrates, or separates into a plurality of incoherent pieces or particles distributed more or less throughout the medium such that no recognizable filaments are recoverable from the medium upon removal of the water, for example, by filtration or evaporation. Thus, "water-dispersible", as used herein, is not intended to include the simple disintegration of an assembly of entangled or bound, but otherwise water insoluble or non-dispersible, fibers wherein the fiber assembly simply breaks apart in water to produce a slurry of fibers in water which could be recovered by removal of the water. In the context of this invention, all of these terms refer to the activity of water or a mixture of water and a water-miscible cosolvent on the sulfopolyesters described herein. Examples of such water-miscible cosolvents includes alcohols, ketones, glycol ethers, esters and the like. It is intended for this terminology to include conditions where the sulfopolyester is dissolved to form a true solution as well as those where the sulfopolyester is dispersed within the aqueous medium. Often, due to the statistical nature of sulfopolyester compositions, it is possible to have a soluble fraction and a dispersed fraction when a single sulfopolyester sample is placed in an aqueous medium.

Similarly, the term "water-dispersible", as used herein in reference to the sulfopolyester as one component of a multi-component fiber or fibrous article, also is intended to be synonymous with the terms "water-dissipatable", "water-disintegratable", "water-dissolvable", "water-dispellable", "water soluble", "water-removable", "hydrosoluble", and "hydrodispersible" and is intended to mean that the sulfopolyester component is sufficiently removed from the multicomponent fiber and is dispersed or dissolved by the action of water to enable the release and separation of the water non-dispersible fibers contained therein. The terms "dispersed", "dispersible", "dissipate", or "dissipatable" mean that, using a sufficient amount of deionized water (e.g., 100:1 water:fiber by weight) to form a loose suspension or slurry of the fibers or fibrous article, at a temperature of about 60° C., and within a time period of up to 5 days, sulfopolyester component dissolves, disintegrates, or separates from the multicomponent fiber, leaving behind a plurality of microdenier fibers from the water non-dispersible segments.

The water-dispersible fiber of the present invention is prepared from polyesters or, more specifically sulfopolyesters, comprising dicarboxylic acid monomer residues, sulfomonomer residues, diol monomer residues, and repeating units. The sulfomonomer may be a dicarboxylic acid, a diol, or hydroxycarboxylic acid. Thus, the term "monomer residue", as used herein, means a residue of a dicarboxylic acid, a diol, or a hydroxycarboxylic acid. A "repeating unit", as used herein, means an organic structure having 2 monomer residues bonded through a carbonyloxy group. The sulfopolyesters of the present invention contain substantially equal molar proportions of acid residues (100 mole %) and diol residues (100 mole %) which react in substantially equal proportions such that the total moles of repeating units is equal to 100 mole %. The mole percentages provided in the present disclosure, therefore, may be based on the total moles of acid residues, the total moles of diol residues, or the total moles of repeating units. For example, a sulfopolyester containing 30 mole % of a sulfomonomer, which may be a dicarboxylic acid, a diol, or hydroxycarboxylic acid, based on the total repeating units, means that the sulfopolyester contains 30 mole % sulfomonomer out of a total of 100 mole % repeating units. Thus, there are 30 moles of sulfomonomer residues among every 100 moles of repeating units. Similarly, a sulfopolyester containing 30 mole % of a dicarboxylic acid sulfomonomer, based on the total acid residues, means the sulfopolyester contains 30 mole % sulfomonomer out of a total of 100 mole % acid residues. Thus, in this latter case, there are 30 moles of sulfomonomer residues among every 100 moles of acid residues.

The sulfopolyesters described herein have an inherent viscosity, abbreviated hereinafter as "Ih.V.", of at least about 0.1 dL/g, preferably about 0.2 to 0.3 dL/g, and most preferably greater than about 0.3 dL/g, measured in a 60/40 parts by weight solution of phenol/tetrachloroethane solvent at 25° C. and at a concentration of about 0.5 g of sulfopolyester in 100 mL of solvent. The term "polyester", as used herein, encompasses both "homopolyesters" and "copolyesters" and means a synthetic polymer prepared by the polycondensation of difunctional carboxylic acids with difunctional hydroxyl compound. As used herein, the term "sulfopolyester" means any polyester comprising a sulfomonomer. Typically the difunctional carboxylic acid is a dicarboxylic acid and the difunctional hydroxyl compound is a dihydric alcohol such as, for example glycols and diols. Alternatively, the difunctional carboxylic acid may be a hydroxy carboxylic acid such as, for example, p-hydroxybenzoic acid, and the difunctional hydroxyl compound may be a aromatic nucleus bearing 2 hydroxy substituents such as, for example, hydroquinone. The term "residue", as used herein, means any organic structure incorporated into the polymer through a polycondensation reaction involving the corresponding monomer. Thus, the dicarboxylic acid residue may be derived from a dicarboxylic acid monomer or its associated acid halides, esters, salts, anhydrides, or mixtures thereof. As used herein, therefore, the term dicarboxylic acid is intended to include dicarboxylic acids and any derivative of a dicarboxylic acid, including its associated acid halides, esters, half-esters, salts, half-salts, anhydrides, mixed anhydrides, or mixtures thereof, useful in a polycondensation process with a diol to make a high molecular weight polyester.

The sulfopolyester of the present invention includes one or more dicarboxylic acid residues. Depending on the type and concentration of the sulfomonomer, the dicarboxylic acid residue may comprise from about 60 to about 100 mole % of the acid residues. Other examples of concentration ranges of dicarboxylic acid residues are from about 60 mole % to about 95 mole %, and about 70 mole % to about 95 mole %. Examples of dicarboxylic acids that may be used include aliphatic dicarboxylic acids, alicyclic dicarboxylic acids, aromatic dicarboxylic acids, or mixtures of two or more of these acids. Thus, suitable dicarboxylic acids include, but are not limited to succinic; glutaric; adipic; azelaic; sebacic; fumaric; maleic; itaconic; 1,3-cyclo-hexanedicarboxylic; 1,4-cyclohexanedicarboxylic; diglycolic; 2,5-norbornane-dicarboxylic; phthalic; terephthalic; 1,4-naphthalenedicarboxylic; 2,5-naphthalenedicarboxylic; diphenic; 4,4'-oxydibenzoic; 4,4'-sulfonyldibenzoic; and isophthalic. The preferred dicarboxylic acid residues are isophthalic, terephthalic, and 1,4-cyclohexanedicarboxylic acids, or if diesters are used, dimethyl terephthalate, dimethyl isophthalate, and dimethyl-1,4-cyclohexane-dicarboxylate with the residues of isophthalic and terephthalic acid being especially preferred. Although the dicarboxylic acid methyl ester is the most preferred embodiment, it is also acceptable to include higher order alkyl esters, such as ethyl, propyl, isopropyl, butyl, and so forth. In addition, aromatic esters, particularly phenyl, also may be employed.

The sulfopolyester includes about 4 to about 40 mole %, based on the total repeating units, of residues of at least one sulfomonomer having 2 functional groups and one or more sulfonate groups attached to an aromatic or cycloaliphatic ring wherein the functional groups are hydroxyl, carboxyl, or a combination thereof. Additional examples of concentration ranges for the sulfomonomer residues are about 4 to about 35 mole %, about 8 to about 30 mole %, and about 8 to about 25 mole %, based on the total repeating units. The sulfomonomer may be a dicarboxylic acid or ester thereof containing a sulfonate group, a diol containing a sulfonate group, or a hydroxy acid containing a sulfonate group. The term "sulfonate" refers to a salt of a sulfonic acid having the structure "—SO$_3$M" wherein M is the cation of the sulfonate salt. The cation of the sulfonate salt may be a metal ion such as Li$^+$, Na$^+$, K$^+$, Mg$^{++}$, Ca$^{++}$, Ni$^{++}$, Fe$^{++}$, and the like. Alternatively, the cation of the sulfonate salt may be non-metallic such as a nitrogenous base as described, for example, in U.S. Pat. No. 4,304,901. Nitrogen-based cations are derived from nitrogen-containing bases, which may be aliphatic, cycloaliphatic, or aromatic compounds. Examples of such nitrogen containing bases include ammonia, dimethylethanolamine, diethanolamine, triethanolamine, pyridine, morpholine, and piperidine. Because monomers containing the nitrogen-based sulfonate salts typically are not thermally stable at conditions required to make the polymers in the melt, the method of this invention for preparing sulfopolyesters containing nitrogen-based sulfonate salt groups is to disperse, dissipate, or dissolve the polymer containing the required amount of sulfonate group in the form of its alkali metal salt in water and then exchange the alkali metal cation for a nitrogen-based cation.

When a monovalent alkali metal ion is used as the cation of the sulfonate salt, the resulting sulfopolyester is completely dispersible in water with the rate of dispersion dependent on the content of sulfomonomer in the polymer, temperature of the water, surface area/thickness of the sulfopolyester, and so forth. When a divalent metal ion is used, the resulting sulfopolyesters are not readily dispersed by cold water but are more easily dispersed by hot water. Utilization of more than one counterion within a single polymer composition is possible and may offer a means to tailor or fine-tune the water-responsivity of the resulting article of manufacture. Examples sulfomonomers residues include monomer residues where the sulfonate salt group is attached to an aromatic acid nucleus, such as, for example, benzene; naphthalene; diphenyl; oxydiphenyl; sulfonyldiphenyl; and methylenediphenyl or cycloaliphatic rings, such as, for example, cyclohexyl; cyclopentyl; cyclobutyl; cycloheptyl; and cyclooctyl. Other examples of sulfomonomer residues which may be used in the present invention are the metal sulfonate salt of sulfophthalic acid, sulfoterephthalic acid, sulfoisophthalic acid, or combinations thereof. Other examples of sulfomonomers which may be used are 5-sodiosulfoisophthalic acid and esters thereof. If the sulfomonomer residue is from 5-sodiosulfoisophthalic acid, typical sulfomonomer concentration ranges are about 4 to about 35 mole %, about 8 to about 30 mole %, and about 8 to 25 mole %, based on the total moles of acid residues.

The sulfomonomers used in the preparation of the sulfopolyesters are known compounds and may be prepared using methods well known in the art. For example, sulfomonomers in which the sulfonate group is attached to an aromatic ring may be prepared by sulfonating the aromatic compound with oleum to obtain the corresponding sulfonic acid and followed by reaction with a metal oxide or base, for example, sodium acetate, to prepare the sulfonate salt. Procedures for preparation of various sulfomonomers are described, for example, in U.S. Pat. Nos. 3,779,993; 3,018,272; and 3,528,947.

It is also possible to prepare the polyester using, for example, a sodium sulfonate salt, and ion-exchange methods to replace the sodium with a different ion, such as zinc, when the polymer is in the dispersed form. This type of ion exchange procedure is generally superior to preparing the polymer with divalent salts insofar as the sodium salts are usually more soluble in the polymer reactant melt-phase.

The sulfopolyester includes one or more diol residues which may include aliphatic, cycloaliphatic, and aralkyl glycols. The cycloaliphatic diols, for example, 1,3- and 1,4-cyclohexanedimethanol, may be present as their pure cis or trans isomers or as a mixture of cis and trans isomers. As used herein, the term "diol" is synonymous with the term "glycol" and means any dihydric alcohol. Examples diols include ethylene glycol; diethylene glycol; triethylene glycol; polyethylene glycols; 1,3-propanediol; 2,4-dimethyl-2-ethyl-hexane-1,3-diol; 2,2-dimethyl-1,3-propanediol; 2-ethyl-2-butyl-1,3-propanediol; 2-ethyl-2-isobutyl-1,3-propanediol; 1,3-butanediol; 1,4-butanediol; 1,5-pentanediol; 1,6-hexanediol; 2,2,4-trimethyl-1,6-hexanediol; thiodiethanol; 1,2-cyclohexanedimethanol; 1,3-cyclohexanedimethanol; 1,4-cyclohexanedimethanol; 2,2,4,4-tetramethyl-1,3-cyclobutanediol; p-xylylenediol, or combinations of one or more of these glycols.

The diol residues may include from about 25 mole % to about 100 mole %, based on the total diol residues, of residue of a poly(ethylene glycol) having a structure

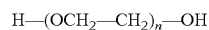

$$H-(OCH_2-CH_2)_n-OH$$

wherein n is an integer in the range of 2 to about 500. Non-limiting examples of lower molecular weight polyethylene glycols, e.g., wherein n is from 2 to 6, are diethylene glycol, triethylene glycol, and tetraethylene glycol. Of these lower molecular weight glycols, diethylene and triethylene glycol are most preferred. Higher molecular weight polyethylene glycols (abbreviated herein as "PEG"), wherein n is from 7 to about 500, include the commercially available products known under the designation CARBOWAX®, a product of Dow Chemical Company (formerly Union Carbide). Typically, PEG's are used in combination with other diols such as, for example, diethylene glycol or ethylene glycol. Based on the values of n, which range from greater than 6 to 500, the molecular weight may range from greater than 300 to about 22,000 g/mol. The molecular weight and the mole % are inversely proportional to each other; specifically, as the molecular weight is increased, the mole % will be decreased in order to achieve a designated degree of hydrophilicity. For example, it is illustrative of this concept to consider that a PEG having a molecular weight of 1000 may constitute up to 10 mole % of the total diol, while a PEG having a molecular weight of 10,000 would typically be incorporated at a level of less than 1 mole % of the total diol.

Certain dimer, trimer, and tetramer diols may be formed in situ due to side reactions that may be controlled by varying the process conditions. For example, varying amounts of diethylene, triethylene, and tetraethylene glycols may be formed from ethylene glycol from an acid-catalyzed dehydration reaction which occurs readily when the polycondensation reaction is carried out under acidic conditions. The presence of buffer solutions, well-known to those skilled in the art, may be added to the reaction mixture to retard these side reactions. Additional compositional latitude is possible, however, if the buffer is omitted and the dimerization, trimerization, and tetramerization reactions are allowed to proceed.

The sulfopolyester of the present invention may include from 0 to about 25 mole %, based on the total repeating units, of residues of a branching monomer having 3 or more functional groups wherein the functional groups are hydroxyl, carboxyl, or a combination thereof. Non-limiting examples of branching monomers are 1,1,1-trimethylol propane, 1,1,1-trimethylolethane, glycerin, pentaerythritol, erythritol, threitol, dipentaerythritol, sorbitol, trimellitic anhydride, pyromellitic dianhydride, dimethylol propionic acid, or combinations thereof. Further examples of branching monomer concentration ranges are from 0 to about 20 mole % and from 0 to about 10 mole %. The presence of a branching monomer may result in a number of possible benefits to the sulfopolyester of the present invention, including but not limited to, the ability to tailor rheological, solubility, and tensile properties. For example, at a constant molecular weight, a branched sulfopolyester, compared to a linear analog, will also have a greater concentration of end groups that may facilitate post-polymerization crosslinking reactions. At high concentrations of branching agent, however, the sulfopolyester may be prone to gelation.

The sulfopolyester used for the fiber of the present invention has a glass transition temperature, abbreviated herein as "Tg", of at least 25° C. as measured on the dry polymer using standard techniques, such as differential scanning calorimetry ("DSC"), well known to persons skilled in the art. The Tg measurements of the sulfopolyesters of the present invention are conducted using a "dry polymer", that is, a polymer sample in which adventitious or absorbed water is driven off by heating to polymer to a temperature of about 200° C. and allowing the sample to return to room temperature. Typically, the sulfopolyester is dried in the DSC apparatus by conducting a first thermal scan in which the sample is heated to a temperature above the water vaporization temperature, holding the sample at that temperature until the vaporization of the water absorbed in the polymer is complete (as indicated by an a large, broad endotherm), cooling the sample to room temperature, and then conducting a second thermal scan to obtain the Tg measurement. Further examples of glass transition temperatures exhibited by the sulfopolyester are at least 30° C., at least 35° C., at least 40° C., at least 50° C., at least 60° C., at least 65° C., at least 80° C., and at least 90° C. Although other Tg's are possible, typical glass transition temperatures of the dry sulfopolyesters our invention are about 30° C., about 48° C., about 55° C., about 65° C., about 70° C., about 75° C., about 85° C., and about 90° C.

Our novel fibers may consist essentially of or, consist of, the sulfopolyesters described hereinabove. In another embodiment, however, the sulfopolyesters of this invention may be a single polyester or may be blended with one or more supplemental polymers to modify the properties of the resulting fiber. The supplemental polymer may or may not be water-dispersible depending on the application and may be miscible or immiscible with the sulfopolyester. If the supplemental polymer is water-nondispersible, it is preferred that the blend with the sulfopolyester is immiscible. The term "miscible", as used herein, is intended to mean that the blend has a single, homogeneous amorphous phase as indicated by a single composition-dependent Tg. For example, a first polymer that is miscible with second polymer may be used to "plasticize" the second polymer as illustrated, for example, in U.S. Pat. No. 6,211,309. By contrast, the term "immiscible", as used herein, denotes a blend that shows at least 2, randomly mixed, phases and exhibits more than one Tg. Some polymers may be immiscible and yet compatible with the sulfopolyester. A further general description of miscible and immiscible polymer blends and the various analytical techniques for their characterization may be found in *Polymer Blends* Volumes 1 and 2, Edited by D. R. Paul and C. B. Bucknall, 2000, John Wiley & Sons, Inc.

Non-limiting examples of water-dispersible polymers that may be blended with the sulfopolyester are polymethacrylic acid, polyvinyl pyrrolidone, polyethylene-acrylic acid copolymers, polyvinyl methyl ether, polyvinyl alcohol, polyethylene oxide, hydroxy propyl cellulose, hydroxypropyl methyl cellulose, methyl cellulose, ethyl hydroxyethyl cellulose, isopropyl cellulose, methyl ether starch, polyacrylamides, poly(N-vinyl caprolactam), polyethyl oxazoline, poly (2-isopropyl-2-oxazoline), polyvinyl methyl oxazolidone, water-dispersible sulfopolyesters, polyvinyl methyl oxazolidimone, poly(2,4-dimethyl-6-triazinylethylene), and ethylene oxide-propylene oxide copolymers. Examples of polymers which are water-nondispersible that may be blended with the sulfopolyester include, but are not limited to, polyolefins, such as homo- and copolymers of polyethylene and polypropylene; poly(ethylene terephthalate); poly(butylene terephthalate); and polyamides, such as nylon-6; polylactides; caprolactone; Eastar Bio® (poly(tetramethylene adipate-co-terephthalate), a product of Eastman Chemical Company); polycarbonate; polyurethane; and polyvinyl chloride.

According to our invention, blends of more than one sulfopolyester may be used to tailor the end-use properties of the resulting fiber or fibrous article, for example, a nonwoven fabric or web. The blends of one or more sulfopolyesters will have Tg's of at least 25° C. for the water-dispersible, unicomponent fibers and at least 57° C. for the multicomponent fibers. Thus, blending may also be exploited to alter the processing characteristics of a sulfopolyester to facilitate the fabrication of a nonwoven. In another example, an immiscible blend of polypropylene and sulfopolyester may provide a conventional nonwoven web that will break apart and completely disperse in water as true solubility is not needed. In this latter example, the desired performance is related to maintaining the physical properties of the polypropylene while the sulfopolyester is only a spectator during the actual use of the product or, alternatively, the sulfopolyester is fugitive and is removed before the final form of the product is utilized.

The sulfopolyester and supplemental polymer may be blended in batch, semicontinuous, or continuous processes. Small scale batches may be readily prepared in any high-intensity mixing devices well-known to those skilled in the art, such as Banbury mixers, prior to melt-spinning fibers. The components may also be blended in solution in an appropriate solvent. The melt blending method includes blending the sulfopolyester and supplemental polymer at a temperature sufficient to melt the polymers. The blend may be cooled and pelletized for further use or the melt blend can be melt spun directly from this molten blend into fiber form. The term "melt" as used herein includes, but is not limited to, merely softening the polyester. For melt mixing methods generally known in the polymers art, see *Mixing and Compounding of Polymers* (I. Manas-Zloczower & Z. Tadmor editors, Carl Hanser Verlag Publisher, 1994, New York, N.Y.).

Our invention also provides a water-dispersible fiber comprising a sulfopolyester having a glass transition temperature (Tg) of at least 25° C., wherein the sulfpolyester comprises: (i) about 50 to about 96 mole % of one or more residues of isophthalic acid or terephthalic acid, based on the total acid residues; (ii) about 4 to about 30 mole %, based on the total acid residues, of a residue of sodiosulfoisophthalic acid; (iii) one or more diol residues wherein at least 25 mole %, based on the total diol residues, is a poly(ethylene glycol) having a structure

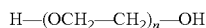

wherein n is an integer in the range of 2 to about 500; (iv) 0 to about 20 mole %, based on the total repeating units, of residues of a branching monomer having 3 or more functional groups wherein the functional groups are hydroxyl, carboxyl, or a combination thereof. As described hereinabove, the fiber may optionally include a first water-dispersible polymer blended with the sulfopolyester; and, optionally, a water-nondispersible polymer blended with the sulfopolyester such that the blend is an immiscible blend. Our fiber contains less than 10 weight percent of a pigment or filler, based on the total weight of the fiber. The first water-dispersible polymer is as described hereinabove. The sulfopolyester should have a glass transition temperature (Tg) of at least 25° C., but may have, for example, a Tg of about 35° C., about 48° C., about 55° C., about 65° C., about 70° C., about 75° C., about 85° C., and about 90° C. The sulfopolyester may contain other concentrations of isophthalic acid residues, for example, about 60 to about 95 mole %, and about 75 to about 95 mole %. Further examples of isophthalic acid residue concentrations ranges are about 70 to about 85 mole %, about 85 to about 95 mole % and about 90 to about 95 mole %. The sulfopolyester also may comprise about 25 to about 95 mole % of the residues of diethylene glycol. Further examples of diethylene glycol residue concentration ranges include about 50 to about 95 mole %, about 70 to about 95 mole %, and about 75 to about 95 mole %. The sulfopolyester also may include the residues of ethylene glycol and/or 1,4-cyclohexanedimethanol, abbreviated herein as "CHDM". Typical concentration ranges of CHDM residues are about 10 to about 75 mole %, about 25 to about 65 mole %, and about 40 to about 60 mole %. Typical concentration ranges of ethylene glycol residues are about 10 to about 75 mole %, about 25 to about 65 mole %, and about 40 to about 60 mole %. In another embodiment, the sulfopolyester comprises is about 75 to about 96 mole % of the residues of isophthalic acid and about 25 to about 95 mole % of the residues of diethylene glycol.

The sulfopolyesters of the instant invention are readily prepared from the appropriate dicarboxylic acids, esters, anhydrides, or salts, sulfomonomer, and the appropriate diol or diol mixtures using typical poly-condensation reaction conditions. They may be made by continuous, semi-continuous, and batch modes of operation and may utilize a variety of reactor types. Examples of suitable reactor types include, but are not limited to, stirred tank, continuous stirred tank, slurry, tubular, wiped-film, falling film, or extrusion reactors. The term "continuous" as used herein means a process wherein reactants are introduced and products withdrawn simultaneously in an uninterrupted manner. By "continuous" it is meant that the process is substantially or completely continuous in operation and is to be contrasted with a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which no material is fed or removed into the reactor. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses. The process is operated advantageously as a continuous process for economic reasons and to produce superior coloration of the polymer as the sulfopolyester may deteriorate in appearance if allowed to reside in a reactor at an elevated temperature for too long a duration.

The sulfopolyesters of the present invention are prepared by procedures known to persons skilled in the art. The sulfomonomer is most often added directly to the reaction mixture from which the polymer is made, although other processes are known and may also be employed, for example, as described in U.S. Pat. Nos. 3,018,272, 3,075,952, and 3,033,822. The reaction of the sulfomonomer, diol component and the dicarboxylic acid component may be carried out using conventional polyester polymerization conditions. For example, when preparing the sulfopolyesters by means of an ester interchange reaction, i.e., from the ester form of the dicarboxylic acid components, the reaction process may comprise two steps. In the first step, the diol component and the dicarboxylic acid component, such as, for example, dimethyl isophthalate, are reacted at elevated temperatures, typically, about 150° C. to about 250° C. for about 0.5 to about 8 hours at pressures ranging from about 0.0 kPa gauge to about 414 kPa gauge (60 pounds per square inch, "psig"). Preferably, the temperature for the ester interchange reaction ranges from about 180° C. to about 230° C. for about 1 to about 4 hours while the preferred pressure ranges from about 103 kPa gauge (15 psig) to about 276 kPa gauge (40 psig). Thereafter, the reaction product is heated under higher temperatures and under reduced pressure to form sulfopolyester with the elimination of diol, which is readily volatilized under these conditions and removed from the system. This second step, or polycondensation step, is continued under higher vacuum and a temperature which generally ranges from about 230° C. to about 350° C., preferably about 250° C. to about 310° C. and most preferably about 260° C. to about 290° C. for about 0.1 to about 6 hours, or preferably, for about 0.2 to about 2 hours, until a polymer having the desired degree of polymerization, as determined by inherent viscosity, is obtained. The polycondensation step may be conducted under reduced pressure which ranges from about 53 kPa (400 torr) to about 0.013 kPa (0.1 torr). Stirring or appropriate conditions are used in both stages to ensure adequate heat transfer and surface renewal of the reaction mixture. The reactions of both stages are facilitated by appropriate catalysts such as, for example, alkoxy titanium compounds, alkali metal hydroxides and alcoholates, salts of organic carboxylic acids, alkyl tin compounds, metal oxides, and the like. A three-stage manufacturing procedure, similar to that described in U.S. Pat. No. 5,290,631, may also be used, particularly when a mixed monomer feed of acids and esters is employed.

To ensure that the reaction of the diol component and dicarboxylic acid component by an ester interchange reaction mechanism is driven to completion, it is preferred to employ about 1.05 to about 2.5 moles of diol component to one mole dicarboxylic acid component. Persons of skill in the art will understand, however, that the ratio of diol component to dicarboxylic acid component is generally determined by the design of the reactor in which the reaction process occurs.

In the preparation of sulfopolyester by direct esterification, i.e., from the acid form of the dicarboxylic acid component, sulfopolyesters are produced by reacting the dicarboxylic acid or a mixture of dicarboxylic acids with the diol component or a mixture of diol components. The reaction is conducted at a pressure of from about 7 kPa gauge (1 psig) to about 1379 kPa gauge (200 psig), preferably less than 689 kPa (100 psig) to produce a low molecular weight, linear or branched sulfopolyester product having an average degree of polymerization of from about 1.4 to about 10. The temperatures employed during the direct esterification reaction typically range from about 180° C. to about 280° C., more preferably ranging from about 220° C. to about 270° C. This low molecular weight polymer may then be polymerized by a polycondensation reaction.

The water dispersible and multicomponent fibers and fibrous articles of this invention also may contain other conventional additives and ingredients which do not deleteriously affect their end use. For example, additives such as fillers, surface friction modifiers, light and heat stabilizers, extrusion aids, antistatic agents, colorants, dyes, pigments, fluorescent brighteners, antimicrobials, anticounterfeiting markers, hydrophobic and hydrophilic enhancers, viscosity modifiers, slip agents, tougheners, adhesion promoters, and the like may be used. The fibers and fibrous articles of our invention do not require the presence of additives such as, for example, pigments, fillers, oils, waxes, or fatty acid finishes, to prevent blocking or fusing of the fibers during processing. The terms "blocking or fusing", as used herein, is understood to mean that the fibers or fibrous articles stick together or fuse into a mass such that the fiber cannot be processed or used for its intended purpose. Blocking and fusing can occur during processing of the fiber or fibrous article or during storage over a period of days or weeks and is exacerbated under hot, humid conditions. In one embodiment of the invention, the fibers and fibrous articles will contain less than 10 wt % of such anti-blocking additives, based on the total weight of the fiber or fibrous article. For example, the fibers and fibrous articles may contain less than 10 wt % of a pigment or filler. In other examples, the fibers and fibrous articles may contain less than 9 wt %, less than 5 wt %, less than 3 wt %, less than 1 wt %, and 0 wt % of a pigment or filler, based on the total weight of the fiber. Colorants, sometimes referred to as toners, may be added to impart a desired neutral hue and/or brightness to the sulfopolyester. When colored fibers are desired, pigments or colorants may be included in the sulfopolyester reaction mixture during the reaction of the diol monomer and the dicarboxylic acid monomer or they may be melt blended with the preformed sulfopolyester. A preferred method of including colorants is to use a colorant having thermally stable organic colored compounds having reactive groups such that the colorant is copolymerized and incorporated into the sulfopolyester to improve its hue. For example, colorants such as dyes possessing reactive hydroxyl and/or carboxyl groups, including, but not limited to, blue and red substituted anthraquinones, may be copolymerized into the polymer chain. When dyes are employed as colorants, they may be added to the copolyester reaction process after an ester interchange or direct esterification reaction.

For the purposes of this invention, the term "fiber" refers to a polymeric body of high aspect ratio capable of being formed into two or three dimensional articles such as woven or non-woven fabrics. In the context of the present invention, the term "fiber" is synonymous with "fibers" and intended to mean one or more fibers. The fibers of our invention may be unicomponent fibers, bicomponent, or multicomponent fibers. The term "unicomponent fiber", as used herein, is intended to mean a fiber prepared by melt spinning a single sulfopolyester, blends of one or more sulfopolyesters, or blends of one or more sulfopolyesters with one or more additional polymers and includes staple, monofilament, and multifilament fibers. "Unicomponent" is intended to be synonymous with the term "monocomponent" and includes "biconstituent" or "multiconstituent" fibers, and refers to fibers which have been formed from at least two polymers extruded from the same extruder as a blend. Unicomponent or biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Thus, the term "unicomponent" is not intended to exclude fibers formed from a polymer or blends of one or more polymers to which small amounts of additives may be added for coloration, anti-static properties, lubrication, hydrophilicity, etc. By contrast, the term "multicomponent fiber", as used herein, intended to mean a fiber prepared by melting the two or more fiber forming polymers in separate extruders and by directing the resulting multiple polymer flows into one spinneret with a plurality of distribution flow paths but spun together to form one fiber. Multicomponent fibers are also sometimes referred to as conjugate or bicomponent fibers. The polymers are arranged in substantially constantly positioned distinct zones across the cross-section of the conjugate fibers and extend continuously along the length of the conjugate fibers. The configuration of such a multicomponent fiber may be, for example, a sheath/core arrangement wherein one polymer is surrounded by another or may be a side by side arrangement, a pie arrangement or an "islands-in-the-sea" arrangement. For example, a multicomponent fiber may be prepared by extruding the sulfopolyester and one or more water non-dispersible polymers separately through a spinneret having a shaped or engineered transverse geometry such as, for example, an "islands-in-the-sea" or segmented pie configuration. Unicomponent fibers, typically, are staple, monofilament or multifilament fibers that have a shaped or round cross-section. Most fiber forms are heatset. The fiber may include the various antioxidants, pigments, and additives as described herein.

Monofilament fibers generally range in size from about 15 to about 8000 denier per filament (abbreviated herein as "d/f"). Our novel fibers typically will have d/f values in the range of about 40 to about 5000. Monofilaments may be in the form of unicomponent or multicomponent fibers. The multifilament fibers of our invention will preferably range in size from about 1.5 micrometers for melt blown webs, about 0.5 to about 50 d/f for staple fibers, and up to about 5000 d/f for monofilament fibers. Multifilament fibers may also be used as crimped or uncrimped yarns and tows. Fibers used in melt blown web and melt spun fabrics may be produced in microdenier sizes. The term "microdenier", as used herein, is intended to mean a d/f value of 1 d/f or less. For example, the microdenier fibers of the instant invention typically have d/f values of 1 or less, 0.5 or less, or 0.1 or less. Nanofibers can also be produced by electrostatic spinning.

As noted hereinabove, the sulfopolyesters also are advantageous for the preparation of bicomponent and multicomponent fibers having a shaped cross section. We have discovered that sulfopolyesters or blends of sulfopolyesters having a glass transition temperature (Tg) of at least 57° C. are particularly useful for multicomponent fibers to prevent blocking and fusing of the fiber during spinning and take up. Thus, our invention provides a multicomponent fiber having shaped cross section, comprising:

A) a water dispersible sulfopolyester having a glass transition temperature (Tg) of at least 57° C., the sulfpolyester comprising:
  (i) residues of one or more dicarboxylic acids;
  (ii) about 4 to about 40 mole %, based on the total repeating units, of residues of at least one sulfomonomer having 2 functional groups and one or more sulfonate groups attached to an aromatic or cycloaliphatic ring wherein the functional groups are hydroxyl, carboxyl, or a combination thereof;
  (iii) one or more diol residues wherein at least 25 mole %, based on the total diol residues, is a poly(ethylene glycol) having a structure

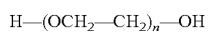

H—(OCH$_2$—CH$_2$)$_n$—OH wherein n is an integer in the range of 2 to about 500; and
  (iv) 0 to about 25 mole %, based on the total repeating units, of residues of a branching monomer having 3 or more functional groups wherein the functional groups are hydroxyl, carboxyl, or a combination thereof; and
B) a plurality of segments comprising one or more water-nondispersable polymers immiscible with the sulfopolyester, wherein the segments are substantially isolated from each other by the sulfopolyester intervening between the segments;
wherein the fiber has an islands-in-the-sea or segmented pie cross section and contains less than 10 weight percent of a pigment or filler, based on the total weight of the fiber.

The dicarboxylic acids, diols, sulfopolyester, sulfomonomers, and branching monomers residues are as described previously for other embodiments of the invention. For multicomponent fibers, it is advantageous that the sulfopolyester have a Tg of at least 57° C. Further examples of glass transition temperatures that may be exhibited by the sulfopolyester or sulfopolyester blend of our multicomponent fiber are at least 60° C., at least 65° C., at least 70° C., at least 75° C., at least 80° C., at least 85° C., and at least 90° C. Further, to obtain a sulfopolyester with a Tg of at least 57° C., blends of one or more sulfopolyesters may be used in varying proportions to obtain a sulfopolyester blend having the desired Tg. The Tg of a sulfopolyester blend may be calculated by using a weighted average of the Tg's of the sulfopolyester components. For example, sulfopolyester having a Tg of 48° C. may be blended in a 25:75 wt:wt ratio with another sulfopolyester having Tg of 65° C. to give a sulfopolyester blend having a Tg of approximately 61° C.

The multicomponent fiber comprises a plurality of segments one or more water-nondispersable polymers immiscible with the sulfopolyester in which the segments are substantially isolated from each other by the sulfopolyester intervening between the segments. The term "substantially isolated", as used herein, is intended to mean that the segments are set apart from each other to permit the segments to form individual fibers upon removal of the sulfopolyester. For example, the segments may be touching each others as in, for example, a segmented pie configuration but can be split apart by impact or when the sulfopolyester is removed.

The ratio by weight of the sulfopolyester to water non-dispersible polymer component in the multicomponent fiber of the invention is generally in the range of about 60:40 to about 2:98 or, in another example, in the range of about 50:50 to about 5:95. Typically, the sulfopolyester comprises 50% by weight or less of the total weight of the multicomponent fiber.

The segments of multicomponent fiber may comprise one of more water non-dispersible polymers. Examples of water-nondispersible polymers which may be used in segments of the multicomponent fiber include, but are not limited to, polyolefins, polyesters, polyamides, polylactides, polycaprolactone, polycarbonate, polyurethane, and polyvinyl chloride. For example, the water non-dispersible polymer may be polyester such as poly(ethylene)terephthalate, poly(butylene) terephthalate, poly(cyclohexylene)cyclohexanedicarboxylate, poly(cyclohexylene)terephthalate, poly(trimethylene)terephthalate, and the like. In another example, the water-nondispersible polymer biodistintegratable as determined by DIN Standard 54900 and/or biodegradable as determined by ASTM Standard Method, D6340-98. Examples of biodegradable polyesters and polyester blends are disclosed in U.S. Pat. Nos. 5,599,858; 5,580,911; 5,446,079; and 5,559,171. The term "biodegradable", as used herein in reference to the water non-dispersible polymers of the present invention, is understood to mean that the polymers are degraded under environmental influences such as, for example, in a composting environment, in an appropriate and demonstrable time span as defined, for example, by ASTM Standard Method, D6340-98, entitled "Standard Test Methods for Determining Aerobic Biodegradation of Radiolabeled Plastic Materials in an Aqueous or Compost Environment". The water non-dispersible polymers of the present invention also may be "biodisintegratable", meaning that the polymers are easily fragmented in a composting environment as defined, for example, by DIN Standard 54900. For example, the biodegradable polymer is initially reduced in molecular weight in the environment by the action of heat, water, air, microbes and other factors. This reduction in molecular weight results in a loss of physical properties (tenacity) and often in fiber breakage. Once the molecular weight of the polymer is sufficiently low, the monomers and oligomers are then assimilated by the microbes. In an aerobic environment, these monomers or oligomers are ultimately oxidized to $CO_2$, $H_2O$, and new cell biomass. In an anaerobic environment, the monomers or oligomers are ultimately converted to $CO_2$, $H_2$, acetate, methane, and cell biomass.

For example, water-nondispersible polymer may be an aliphatic-aromatic polyester, abbreviated herein as "AAPE". The term "aliphatic-aromatic polyester", as used herein, means a polyester comprising a mixture of residues from aliphatic or cycloaliphatic dicarboxylic acids or diols and aromatic dicarboxylic acids or diols. The term "non-aromatic", as used herein with respect to the dicarboxylic acid and diol monomers of the present invention, means that carboxyl or hydroxyl groups of the monomer are not connected through an aromatic nucleus. For example, adipic acid contains no aromatic nucleus in its backbone, i.e., the chain of carbon atoms connecting the carboxylic acid groups, thus is "non-aromatic". By contrast, the term "aromatic" means the dicarboxylic acid or diol contains an aromatic nucleus in the backbone such as, for example, terephthalic acid or 2,6-naphthalene dicarboxylic acid. "Non-aromatic", therefore, is intended to include both aliphatic and cycloaliphatic structures such as, for example, diols and dicarboxylic acids, which contain as a backbone a straight or branched chain or cyclic arrangement of the constituent carbon atoms which may be saturated or paraffinic in nature, unsaturated, i.e., containing non-aromatic carbon-carbon double bonds, or acetylenic, i.e., containing carbon-carbon triple bonds. Thus, in the context of the description and the claims of the present invention, non-aromatic is intended to include linear and branched, chain structures (referred to herein as "aliphatic") and cyclic structures (referred to herein as "alicyclic" or "cycloaliphatic"). The term "non-aromatic", however, is not intended to exclude any aromatic substituents which may be attached to the backbone of an aliphatic or cycloaliphatic diol or dicarboxylic acid. In the present invention, the difunctional carboxylic acid typically is a aliphatic dicarboxylic acid such as, for example, adipic acid, or an aromatic dicarboxylic acid such as, for example, terephthalic acid. The difunctional hydroxyl compound may be cycloaliphatic diol such as, for example, 1,4-cyclohexanedimethanol, a linear or branched aliphatic diol such as, for example, 1,4-butanediol, or an aromatic diol such as, for example, hydroquinone.

The AAPE may be a linear or branched random copolyester and/or chain extended copolyester comprising diol residues which comprise the residues of one or more substituted or unsubstituted, linear or branched, diols selected from aliphatic diols containing 2 to about 8 carbon atoms, polyalkylene ether glycols containing 2 to 8 carbon atoms, and cycloaliphatic diols containing about 4 to about 12 carbon atoms. The substituted diols, typically, will comprise 1 to about 4 substituents independently selected from halo, $C_6$-$C_{10}$ aryl, and $C_1$-$C_4$ alkoxy. Examples of diols which may be used include, but are not limited to, ethylene glycol, diethylene glycol, propylene glycol, 1,3-propanediol, 2,2-dimethyl-1,3-propanediol, 1,3-butanediol, 1,4-butanediol, 1,5-pentanediol, 1,6-hexanediol, polyethylene glycol, diethylene glycol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, triethylene glycol, and tetraethylene glycol with the preferred diols comprising one or more diols selected from 1,4-butanediol; 1,3-propanediol; ethylene glycol; 1,6-hexanediol; diethylene glycol; or 1,4-cyclohexanedimethanol. The AAPE also comprises diacid residues which contain about 35 to about 99 mole %, based on the total moles of diacid residues, of the residues of one or more substituted or unsubstituted, linear or branched, non-aromatic dicarboxylic acids selected from aliphatic dicarboxylic acids containing 2 to about 12 carbon atoms and cycloaliphatic acids containing about 5 to about 10 carbon atoms. The substituted non-aromatic dicarboxylic acids will typically contain 1 to about 4 substituents selected from halo, $C_6$-$C_{10}$ aryl, and $C_1$-$C_4$ alkoxy. Non-limiting examples of non-aromatic diacids include malonic, succinic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, and 2,5-norbornanedicarboxylic. In addition to the non-aromatic dicarboxylic acids, the AAPE comprises about 1 to about 65 mole %, based on the total moles of diacid residues, of the residues of one or more substituted or unsubstituted aromatic dicarboxylic acids containing 6 to about 10 carbon atoms. In the case where substituted aromatic dicarboxylic acids are used, they will typically contain 1 to about 4 substituents selected from halo, $C_6$-$C_{10}$ aryl, and $C_1$-$C_4$ alkoxy. Non-limiting examples of aromatic dicarboxylic acids which may be used in the AAPE of our invention are terephthalic acid, isophthalic acid, salts of 5-sulfoisophthalic acid, and 2,6-naphthalenedicarboxylic acid. More preferably, the non-aromatic dicarboxylic acid will comprise adipic acid, the aromatic dicarboxylic acid will comprise terephthalic acid, and the diol will comprise 1,4-butanediol.

Other possible compositions for the AAPE's of our invention are those prepared from the following diols and dicarboxylic acids (or polyester-forming equivalents thereof such as diesters) in the following mole percentages, based on 100 mole percent of a diacid component and 100 mole percent of a diol component:

(1) glutaric acid (about 30 to about 75%); terephthalic acid (about 25 to about 70%); 1,4-butanediol (about 90 to 100%); and modifying diol (0 about 10%);

(2) succinic acid (about 30 to about 95%); terephthalic acid (about 5 to about 70%); 1,4-butanediol (about 90 to 100%); and modifying diol (0 to about 10%); and (3) adipic acid (about 30 to about 75%); terephthalic acid (about 25 to about 70%); 1,4-butanediol (about 90 to 100%); and modifying diol (0 to about 10%).

The modifying diol preferably is selected from 1,4-cyclohexanedimethanol, triethylene glycol, polyethylene glycol and neopentyl glycol. The most preferred AAPE's are linear, branched or chain extended copolyesters comprising about 50 to about 60 mole percent adipic acid residues, about 40 to about 50 mole percent terephthalic acid residues, and at least 95 mole percent 1,4-butanediol residues. Even more preferably, the adipic acid residues comprise about 55 to about 60 mole percent, the terephthalic acid residues comprise about 40 to about 45 mole percent, and the diol residues comprise about 95 mole percent 1,4-butanediol residues. Such compositions are commercially available under the trademark EASTAR BIO® copolyester from Eastman Chemical Company, Kingsport, Tenn., and under the trademark ECOFLEX® from BASF Corporation.

Additional, specific examples of preferred AAPE's include a poly(tetramethylene glutarate-co-terephthalate) containing (a) 50 mole percent glutaric acid residues, 50 mole percent terephthalic acid residues, and 100 mole percent 1,4-butanediol residues, (b) 60 mole percent glutaric acid residues, 40 mole percent terephthalic acid residues, and 100 mole percent 1,4-butanediol residues or (c) 40 mole percent glutaric acid residues, 60 mole percent terephthalic acid residues, and 100 mole percent 1,4-butanediol residues; a poly(tetramethylene succinate-co-terephthalate) containing (a) 85 mole percent succinic acid residues, 15 mole percent terephthalic acid residues, and 100 mole percent 1,4-butanediol residues or (b) 70 mole percent succinic acid residues, 30 mole percent terephthalic acid residues, and 100 mole percent 1,4-butanediol residues; a poly(ethylene succinate-co-terephthalate) containing 70 mole percent succinic acid residues, 30 mole percent terephthalic acid residues, and 100 mole percent ethylene glycol residues; and a poly(tetramethylene adipate-co-terephthalate) containing (a) 85 mole percent adipic acid residues, 15 mole percent terephthalic acid residues, and 100 mole percent 1,4-butanediol residues; or (b) 55 mole percent adipic acid residues, 45 mole percent terephthalic acid residues, and 100 mole percent 1,4-butanediol residues.

The AAPE preferably comprises from about 10 to about 1,000 repeating units and preferably, from about 15 to about 600 repeating units. The AAPE may have an inherent viscosity of about 0.4 to about 2.0 dL/g, or more preferably about 0.7 to about 1.6 dL/g, as measured at a temperature of 25° C. using a concentration of 0.5 gram copolyester in 100 ml of a 60/40 by weight solution of phenol/tetrachloroethane.

The AAPE, optionally, may contain the residues of a branching agent. The mole percentage ranges for the branching agent are from about 0 to about 2 mole %, preferably about 0.1 to about 1 mole %, and most preferably about 0.1 to about 0.5 mole % based on the total moles of diacid or diol residues (depending on whether the branching agent contains carboxyl or hydroxyl groups). The branching agent preferably has a weight average molecular weight of about 50 to about 5000, more preferably about 92 to about 3000, and a functionality of about 3 to about 6. The branching agent, for example, may be the esterified residue of a polyol having 3 to 6 hydroxyl groups, a polycarboxylic acid having 3 or 4 carboxyl groups (or ester-forming equivalent groups) or a hydroxy acid having a total of 3 to 6 hydroxyl and carboxyl groups. In addition, the AAPE may be branched by the addition of a peroxide during reactive extrusion.

Each segment of the water non-dispersible polymer may be different from others in fineness and may be arranged in any shaped or engineered cross-sectional geometry known to persons skilled in the art. For example, the sulfopolyester and a water-nondispersible polymer may be used to prepare a bicomponent fiber having an engineered geometry such as, for example, a side-by-side, "islands-in-the-sea", segmented pie, other splitables, sheath/core, or other configurations known to persons skilled in the art. Other multicomponent configurations are also possible. Subsequent removal of a side, the "sea", or a portion of the "pie" can result in very fine fibers. The process of preparing bicomponent fibers also is well known to persons skilled in the art. In a bicomponent fiber, the sulfopolyester fibers of this invention may be present in amounts of about 10 to about 90 weight % and will generally be used in the sheath portion of sheath/core fibers. The other component may be from a wide range of other polymeric materials such as, for example, poly(ethylene) terephthalate, poly(butylene)terephthalate, poly(trimethylene)terephthalate, polylactides and the like as well as polyolefins, cellulose esters, and polyamides. Typically, when a water-insoluble or water-nondispersible polymer is used, the resulting bicomponent or multicomponent fiber is not completely water-dispersible. Side by side combinations with significant differences in thermal shrinkage can be utilized for the development of a spiral crimp. If crimping is desired, a saw tooth or stuffer box crimp is generally suitable for many applications. If the second polymer component is in the core of a sheath/core configuration, such a core optionally may be stabilized.

The sulfopolyesters are particularly useful for fibers having an "islands-in-the-sea" or "segmented pie" cross section as they only requires neutral or slightly acidic (i.e., "soft" water) to disperse, as compared to the caustic-containing solutions that are sometimes required to remove other water dispersible polymers from multicomponent fibers. Thus another aspect of our invention is a multicomponent fiber, comprising:

A) a water dispersible sulfopolyester having a glass transition temperature (Tg) of at least 57° C., the sulfopolyester comprising:
  (i) about 50 to about 96 mole % of one or more residues of isophthalic acid or terephthalic acid, based on the total acid residues;
  (ii) about 4 to about 30 mole %, based on the total acid residues, of a residue of sodiosulfoisophthalic acid;
  (iii) one or more diol residues wherein at least 25 mole %, based on the total diol residues, is a poly(ethylene glycol) having a structure H—(OCH$_2$—CH$_2$)$_n$—OH wherein n is an integer in the range of 2 to about 500;
  (iv) 0 to about 20 mole %, based on the total repeating units, of residues of a branching monomer having 3 or more functional groups wherein the functional groups are hydroxyl, carboxyl, or a combination thereof; and
(B) a plurality of segments comprising one or more water-nondispersible polymers immiscible with the sulfopolyester, wherein the segments are substantially isolated from each other by the sulfopolyester intervening between the segments;
wherein the fiber has an islands-in-the-sea or segmented pie cross section and contains less than 10 weight percent of a pigment or filler, based on the total weight of the fiber.

The dicarboxylic acids, diols, sulfopolyester, sulfomonomers, branching monomers residues, and water non-dispersible polymers are as described previously. For multicomponent fibers, it is advantageous that sulfopolyester have a Tg of at least 57° C. The sulfopolyester may be a single sulfopolyester or a blend of one or more sulfopolyester polymers. Further examples of glass transition temperatures that may be exhibited by the sulfopolyester or sulfopolyester blends are at least 65° C., at least 70° C., at least 75° C., at least 85° C., and at least 90° C. For example, the sulfopolyester may comprise about 75 to about 96 mole % of one or more residues of isophthalic acid or terephthalic acid and about 25 to about 95 mole % of a residue of diethylene glycol. As described hereinabove, examples of the water-nondispersible polymers are polyolefins, polyesters, polyamides, polylactides, polycaprolactone, polycarbonate, polyurethane, and polyvinyl chloride. In addition, the water-nondispersible polymer may be biodegradable or biodisintegratable. For example, the water-nondispersible polymer may be an aliphatic-aromatic polyester as described previously.

Our novel multicomponent fiber may be prepared by any number of methods known to persons skilled in the art. The present invention thus provides a process for a multicomponent fiber having a shaped cross section comprising: spinning a water dispersible sulfopolyester having a glass transition temperature (Tg) of at least 57° C. and one or more water-nondispersable polymers immiscible with the sulfopolyester into a fiber, the sulfopolyester comprising:
(i) residues of one or more dicarboxylic acids;
(ii) about 4 to about 40 mole %, based on the total repeating units, of residues of at least one sulfomonomer having 2 functional groups and one or more sulfonate groups attached to an aromatic or cycloaliphatic ring wherein the functional groups are hydroxyl, carboxyl, or a combination thereof;
(iii) one or more diol residues wherein at least 25 mole %, based on the total diol residues, is a poly(ethylene glycol) having a structure H—(OCH$_2$—CH$_2$)$_n$—OH wherein n is an integer in the range of 2 to about 500; and
(iv) 0 to about 25 mole %, based on the total repeating units, of residues of a branching monomer having 3 or more functional groups wherein the functional groups are hydroxyl, carboxyl, or a combination thereof;
wherein the fiber has a plurality of segments comprising the water-nondispersable polymers and the segments are substantially isolated from each other by the sulfopolyester intervening between the segments and the fiber contains less than 10 weight percent of a pigment or filler, based on the total weight of the fiber. For example, the multicomponent fiber may be prepared by melting the sulfopolyester and one or more water non-dispersible polymers in separate extruders and directing the individual polymer flows into one spinneret or extrusion die with a plurality of distribution flow paths such that the water non-dispersible polymer component form small segments or thin strands which are substantially isolated from each other by the intervening sulfopolyester. The cross section of such a fiber may be, for example, a segmented pie arrangement or an islands-in-the-sea arrangement. In another example, the sulfopolyester and one or more water non-dispersible polymers are separately fed to the spinneret orifices and then extruded in sheath-core form in which the water non-dispersible polymer forms a "core" that is substantially enclosed by the sulfopolyester "sheath" polymer. In the case of such concentric fibers, the orifice supplying the "core" polymer is in the center of the spinning orifice outlet and flow conditions of core polymer fluid are strictly controlled to maintain the concentricity of both components when spinning. Modifications in spinneret orifices enable different shapes of core and/or sheath to be obtained within the fiber cross-section. In yet another example, a multicomponent fiber having a side-by-side cross section or configuration may be produced by coextruding the water dispersible sulfopolyester and water non-dispersible polymer through orifices separately and converging the separate polymer streams at substantially the same speed to merge side-by-side as a combined stream below the face of the spinneret; or (2) by feeding the two polymer streams separately through orifices, which converge at the surface of the spinneret, at substantially the same speed to merge side-by-side as a combined stream at the surface of the spinneret. In both cases, the velocity of each polymer stream, at the point of merge, is determined by its metering pump speed, the number of orifices, and the size of the orifice.

The dicarboxylic acids, diols, sulfopolyester, sulfomonomers, branching monomers residues, and water non-dispersible polymers are as described previously. The sulfopolyester has a glass transition temperature of at least 60° C. Further examples of glass transition temperatures that may be exhibited by the sulfopolyester or sulfopolyester blend are at least 65° C., at least 70° C., at least 75° C., at least 85° C., and at least 90° C. In one example, the sulfopolyester may comprise about 50 to about 96 mole % of one or more residues of isophthalic acid or terephthalic acid, based on the total acid residues; and about 4 to about 30 mole %, based on the total acid residues, of a residue of sodiosulfoisophthalic acid; and 0 to about 20 mole %, based on the total repeating units, of residues of a branching monomer having 3 or more functional groups wherein the functional groups are hydroxyl, carboxyl, or a combination thereof. In another example, the sulfopolyester may comprise about 75 to about 96 mole % of one or more residues of isophthalic acid or terephthalic acid and about 25 to about 95 mole % of a residue of diethylene glycol. As described hereinabove, examples of the water-nondispersible polymers are polyolefins, polyesters, polyamides, polylactides, polycaprolactone, polycarbonate, polyurethane, and polyvinyl chloride. In addition, the water-nondispersible polymer may be biodegradable or biodisintegratable. For example, the water-nondispersible polymer may be an aliphatic-aromatic polyester as described previously. Examples of shaped cross sections include, but are not limited to, islands-in-the-sea, side-by-side, sheath-core, or segmented pie configurations.

Typically, upon exiting the spinneret, the fibers are quenched with a cross flow of air whereupon the fibers solidify. Various finishes and sizes may be applied to the fiber at this stage. The cooled fibers, typically, are subsequently drawn and wound up on a take up spool. Other additives may be incorporated in the finish in effective amounts like emulsifiers, antistatics, antimicrobials, antifoams, lubricants, thermostabilizers, UV stabilizers, and the like.

Optionally, the drawn fibers may be textured and wound-up to form a bulky continuous filament. This one-step technique is known in the art as spin-draw-texturing. Other embodiments include flat filament (non-textured) yarns, or cut staple fiber, either crimped or uncrimped.

The sulfopolyester may be later removed by dissolving the interfacial layers or pie segments and leaving the smaller filaments or microdenier fibers of the water non-dispersible polymer(s). Our invention thus provides a process for microdenier fibers comprising:

A. spinning a water dispersible sulfopolyester having a glass transition temperature (Tg) of at least 57° C. and one or more water-nondispersable polymers immiscible with the sulfopolyester into multicomponent fibers, the sulfopolyester comprising:
  (i) about 50 to about 96 mole % of one or more residues of isophthalic acid or terephthalic acid, based on the total acid residues;
  (ii) about 4 to about 30 mole %, based on the total acid residues, of a residue of sodiosulfoisophthalic acid;
  (iii) one or more diol residues wherein at least 25 mole %, based on the total diol residues, is a poly(ethylene glycol) having a structure

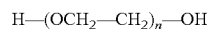

wherein n is an integer in the range of 2 to about 500; and
  (iv) 0 to about 20 mole %, based on the total repeating units, of residues of a branching monomer having 3 or more functional groups wherein the functional groups are hydroxyl, carboxyl, or a combination thereof;
  wherein the fibers have a plurality of segments comprising the water-nondispersable polymers wherein the segments are substantially isolated from each other by the sulfopolyester intervening between the segments and the fibers contain less than 10 weight percent of a pigment or filler, based on the total weight of the fibers; and
B. contacting the multicomponent fibers with water to remove the sulfopolyester thereby forming microdenier fibers.

Typically, the multicomponent fiber is contacted with water at a temperature of about 25° C. to about 100° C., preferably about 50° C. to about 80° C. for a time period of from about 10 to about 600 seconds whereby the sulfopolyester is dissipated or dissolved. After removal of the sulfopolyester, the remaining microfibers typically will have an average fineness of 1 d/f or less, typically, 0.5 d/f or less, or more typically, 0.1 d/f or less. Typical applications of these remaining microfibers include artificial leathers, suedes, wipes, and filter media. The ionic nature of sulfopolyesters also results in advantageously poor "solubility" in saline media, such as body fluids. Such properties are desirable in personal care products and cleaning wipes that are flushable or otherwise disposed in sanitary sewage systems. Selected sulfopolyesters have also been utilized as dispersing agents in dye baths and soil redeposition preventative agents during laundry cycles.

The instant invention also includes a fibrous article comprising the water-dispersible fiber, the multicomponent fiber, or the microdenier fibers described hereinabove. The term "fibrous article" is understood to mean any article having or resembling fibers. Non-limiting examples of fibrous articles include multifilament fibers, yarns, cords, tapes, fabrics, melt blown webs, spunbonded webs, thermobonded webs, hydroentangled webs, nonwoven webs and fabrics, and combinations thereof; items having one or more layers of fibers, such as, for example, multilayer nonwovens, laminates, and composites from such fibers, gauzes, bandages, diapers, training pants, tampons, surgical gowns and masks, feminine napkins; and the like. Further, the fibrous articles may include replacement inserts for various personal hygiene and cleaning products. The fibrous article of the present invention may be bonded, laminated, attached to, or used in conjunction with other materials which may or may not be water-dispersible. The fibrous article, for example, a nonwoven fabric layer, may be bonded to a flexible plastic film or backing of a water-nondispersible material, such as polyethylene. Such an assembly, for example, could be used as one component of a disposable diaper. In addition, the fibrous article may result from overblowing fibers onto another substrate to form highly assorted combinations of engineered melt blown, spunbond, film, or membrane structures.

The fibrous articles of the instant invention include nonwoven fabrics and webs. A nonwoven fabric is defined as a fabric made directly from fibrous webs without weaving or knitting operations. For example, the multicomponent fiber of the present invention may be formed into a fabric by any known fabric forming process like knitting, weaving, needle punching, and hydroentangling. The resulting fabric or web may be converted into a microdenier fiber web by exerting sufficient force to cause the multicomponent fibers to split or by contacting the web with water to remove the sulfopolyester leaving the remaining microdenier fibers behind. Our invention thus provides a process for a microdenier fiber web, comprising:

A. spinning a water dispersible sulfopolyester having a glass transition temperature (Tg) of at least 57° C. and one or more water-nondispersable polymers immiscible with the sulfopolyester into multicomponent fibers, the sulfopolyester comprising:
  (i) about 50 to about 96 mole % of one or more residues of isophthalic acid or terephthalic acid, based on the total acid residues;
  (ii) about 4 to about 30 mole %, based on the total acid residues, of a residue of sodiosulfoisophthalic acid;
  (iii) one or more diol residues wherein at least 25 mole %, based on the total diol residues, is a poly(ethylene glycol) having a structure

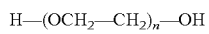

wherein n is an integer in the range of 2 to about 500; and
  (iv) 0 to about 20 mole %, based on the total repeating units, of residues of a branching monomer having 3 or more functional groups wherein the functional groups are hydroxyl, carboxyl, or a combination thereof.
  wherein the multicomponent fibers have a plurality of segments comprising the water-nondispersable polymers wherein the segments are substantially isolated from each other by the sulfopolyester intervening between the segments; and the fiber contains less than 10 weight percent of a pigment or filler, based on the total weight of the fiber;

B. overlapping and collecting the multicomponent fibers of Step A to form a nonwoven web; and C. contacting the nonwoven web with water to remove the sulfopolyester thereby forming a microdenier fiber web.

The nonwoven assembly is held together by 1) mechanical fiber cohesion and interlocking in a web or mat; 2) various techniques of fusing of fibers, including the use of binder fibers, utilizing the thermoplastic properties of certain polymers and polymer blends; 3) use of a binding resin such as starch, casein, a cellulose derivative, or a synthetic resin, such as an acrylic latex or urethane; 4) powder adhesive binders; or 5) combinations thereof. The fibers are often deposited in a random manner, although orientation in one direction is possible, followed by bonding using one of the methods described above.

The fibrous articles of our invention further also may comprise one or more layers of water-dispersible fibers, multicomponent fibers, or microdenier fibers. The fiber layers may be one or more nonwoven fabric layers, a layer of loosely bound overlapping fibers, or a combination thereof. In addition, the fibrous articles may include personal and health care products such as, but not limited to, child care products, such as infant diapers; child training pants; adult care products, such as adult diapers and adult incontinence pads; feminine care products, such as feminine napkins, panty liners, and tampons; wipes; fiber-containing cleaning products; medical and surgical care products, such as medical wipes, tissues, gauzes, examination bed coverings, surgical masks, gowns, bandages, and wound dressings; fabrics; elastomeric yarns, wipes, tapes, other protective barriers, and packaging material. The fibrous articles may be used to absorb liquids or may be pre-moistened with various liquid compositions and used to deliver these compositions to a surface. Non-limiting examples of liquid compositions include detergents; wetting agents; cleaning agents; skin care products, such as cosmetics, ointments, medications, emollients, and fragrances. The fibrous articles also may include various powders and particulates to improve absorbency or as delivery vehicles. Examples of powders and particulates include, but are not limited to, talc, starches, various water absorbent, water-dispersible, or water swellable polymers, such as super absorbent polymers, sulfopolyesters, and poly(vinylalcohols), silica, pigments, and microcapsules. Additives may also be present, but are not required, as needed for specific applications. Examples of additives include, but are not limited to, oxidative stabilizers, UV absorbers, colorants, pigments, opacifiers (delustrants), optical brighteners, fillers, nucleating agents, plasticizers, viscosity modifiers, surface modifiers, antimicrobials, disinfectants, cold flow inhibitors, branching agents, and catalysts.

In addition to being water-dispersible, the fibrous articles described above may be flushable. The term "flushable" as used herein means capable of being flushed in a conventional toilet, and being introduced into a municipal sewage or residential septic system, without causing an obstruction or blockage in the toilet or sewage system.

The fibrous article may further comprise a water-dispersible film comprising a second water-dispersible polymer. The second water-dispersible polymer may be the same as or different from the previously described water-dispersible polymers used in the fibers and fibrous articles of the present invention. In one embodiment, for example, the second water-dispersible polymer may be an additional sulfopolyester which, in turn, comprises: (i) about 50 to about 96 mole % of one or more residues of isophthalic acid or terephthalic acid, based on the total acid residues; (ii) about 4 to about 30 mole %, based on the total acid residues, of a residue of sodiosulfoisophthalic acid; (iii) one or more diol residues wherein at least 15 mole %, based on the total diol residues, is a poly(ethylene glycol) having a structure

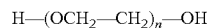

wherein n is an integer in the range of 2 to about 500; (iv) 0 to about 20 mole %, based on the total repeating units, of residues of a branching monomer having 3 or more functional groups wherein the functional groups are hydroxyl, carboxyl, or a combination thereof. The additional sulfopolyester may be blended with one or more supplemental polymers, as described hereinabove, to modify the properties of the resulting fibrous article. The supplemental polymer may or may not be water-dispersible depending on the application. The supplemental polymer may be miscible or immiscible with the additional sulfopolyester.

The additional sulfopolyester may contain other concentrations of isophthalic acid residues, for example, about 60 to about 95 mole %, and about 75 to about 95 mole %. Further examples of isophthalic acid residue concentrations ranges are about 70 to about 85 mole %, about 85 to about 95 mole % and about 90 to about 95 mole %. The additional sulfopolyester also may comprise about 25 to about 95 mole % of the residues of diethylene glycol. Further examples of diethylene glycol residue concentration ranges include about 50 to about 95 mole %, about 70 to about 95 mole %, and about 75 to about 95 mole %. The additional sulfopolyester also may include the residues of ethylene glycol and/or 1,4-cyclohexanedimethanol. Typical concentration ranges of CHDM residues are about 10 to about 75 mole %, about 25 to about 65 mole %, and about 40 to about 60 mole %. Typical concentration ranges of ethylene glycol residues are about 10 to about 75 mole %, about 25 to about 65 mole %, and about 40 to about 60 mole %. In another embodiment, the additional sulfopolyester comprises is about 75 to about 96 mole % of the residues of isophthalic acid and about 25 to about 95 mole % of the residues of diethylene glycol.

According to the invention, the sulfopolyester film component of the fibrous article may be produced as a monolayer or multilayer film. The monolayer film may be produced by conventional casting techniques. The multilayered films may be produced by conventional lamination methods or the like. The film may be of any convenient thickness, but total thickness will normally be between about 2 and about 50 mil.

The film-containing fibrous articles may include one or more layers of water-dispersible fibers as described above. The fiber layers may be one or more nonwoven fabric layers, a layer of loosely bound overlapping fibers, or a combination thereof. In addition, the film-containing fibrous articles may include personal and health care products as described hereinabove.

As described previously, the fibrous articles also may include various powders and particulates to improve absorbency or as delivery vehicles. Thus, in one embodiment, our fibrous article comprises a powder comprising a third water-dispersible polymer that may be the same as or different from the water-dispersible polymer components described previously herein. Other examples of powders and particulates include, but are not limited to, talc, starches, various water absorbent, water-dispersible, or water swellable polymers, such as poly(acrylonitriles), sulfopolyesters, and poly(vinyl alcohols), silica, pigments, and microcapsules.

Our novel fiber and fibrous articles have many possible uses in addition to the applications described above. One novel application involves the melt blowing a film or nonwoven fabric onto flat, curved, or shaped surfaces to provide a protective layer. One such layer might provide surface protection to durable equipment during shipping. At the destination, before putting the equipment into service, the outer layers of sulfopolyester could be washed off. A further embodiment of this general application concept could involve articles of personal protection to provide temporary barrier layers for some reusable or limited use garments or coverings. For the military, activated carbon and chemical absorbers could be sprayed onto the attenuating filament pattern just prior to the collector to allow the melt blown matrix to anchor these entities on the exposed surface. The chemical absorbers can even be changed in the forward operations area as the threat evolves by melt blowing on another layer.

A major advantage inherent to sulfopolyesters is the facile ability to remove or recover the polymer from aqueous dispersions via flocculation or precipitation by adding ionic moieties (i.e., salts). Other methods, such as pH adjustment, adding nonsolvents, freezing, and so forth may also be employed. Therefore, fibrous articles, such as outer wear protective garments, after successful protective barrier use and even if the polymer is rendered as hazardous waste, can potentially be handled safely at much lower volumes for disposal using accepted protocols, such as incineration.

Undissolved or dried sulfopolyesters are known to form strong adhesive bonds to a wide array of substrates, including, but not limited to fluff pulp, cotton, acrylics, rayon, lyocell, PLA (polylactides), cellulose acetate, cellulose acetate propionate, poly(ethylene)terephthalate, poly(butylene)terephthalate, poly(trimethylene)terephthalate, poly(cyclohexylene)terephthalate, copolyesters, polyamides (nylons), stainless steel, aluminum, treated polyolefins, PAN (polyacrylonitriles), and polycarbonates. Thus, our nonwoven fabrics may be used as laminating adhesives or binders that may be bonded by known techniques, such as thermal, radio frequency (RF), microwave, and ultrasonic methods. Adaptation of sulfopolyesters to enable RF activation is disclosed in a number of recent patents. Thus, our novel nonwoven fabrics may have dual or even multifunctionality in addition to adhesive properties. For example, a disposable baby diaper could be obtained where a nonwoven of the present invention serves as both an water-responsive adhesive as well as a fluid managing component of the final assembly.

Our invention also provides a process for water-dispersible fibers comprising (I) heating a water-dispersible polymer composition to a temperature above its flow point, wherein the polymer composition comprises (i) residues of one or more dicarboxylic acids; (ii) about 4 to about 40 mole %, based on the total repeating units, of residues of at least one sulfomonomer having 2 functional groups and one or more metal sulfonate groups attached to an aromatic or cycloaliphatic ring wherein the functional groups are hydroxyl, carboxyl, or a combination thereof; and (iii) one or more diol residues wherein at least 20 mole %, based on the total diol residues, is a poly(ethylene glycol) having a structure

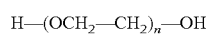

$$H-(OCH_2-CH_2)_n-OH$$

wherein n is an integer in the range of 2 to about 500; (iv) 0 to about 25 mole %, based on the total repeating units, of residues of a branching monomer having 3 or more functional groups wherein the functional groups are hydroxyl, carboxyl, or a combination thereof; wherein the polymer composition contains less than 10 weight percent of a pigment or filler, based on the total weight of the polymer composition; and (II) melt spinning filaments. As described hereinabove, a water-dispersible polymer, optionally, may be blended with the sulfopolyester. In addition, a water-nondispersible polymer, optionally, may be blended with the sulfopolyester to form a blend such that blend is an immiscible blend. The term "flow point", as used herein, means the temperature at which the viscosity of the polymer composition permits extrusion or other forms of processing through a spinneret or extrusion die. The dicarboxylic acid residue may comprise from about 60 to about 100 mole % of the acid residues depending on the type and concentration of the sulfomonomer. Other examples of concentration ranges of dicarboxylic acid residues are from about 60 mole % to about 95 mole % and about 70 mole % to about 95 mole %. The preferred dicarboxylic acid residues are isophthalic, terephthalic, and 1,4-cyclohexanedicarboxylic acids or if diesters are used, dimethyl terephthalate, dimethyl isophthalate, and dimethyl-1,4-cyclohexanedicarboxylate with the residues of isophthalic and terephthalic acid being especially preferred.

The sulfomonomer may be a dicarboxylic acid or ester thereof containing a sulfonate group, a diol containing a sulfonate group, or a hydroxy acid containing a sulfonate group. Additional examples of concentration ranges for the sulfomonomer residues are about 4 to about 25 mole %, about 4 to about 20 mole %, about 4 to about 15 mole %, and about 4 to about 10 mole %, based on the total repeating units. The cation of the sulfonate salt may be a metal ion such as Li$^+$, Na$^+$, K$^+$, Mg$^{++}$, Ca$^{++}$, Ni$^{++}$, Fe$^{++}$, and the like. Alternatively, the cation of the sulfonate salt may be non-metallic such as a nitrogenous base as described previously. Examples of sulfomonomer residues which may be used in the process of the present invention are the metal sulfonate salt of sulfophthalic acid, sulfoterephthalic acid, sulfoisophthalic acid, or combinations thereof. Another example of sulfomonomer which may be used is 5-sodiosulfoisophthalic acid or esters thereof. If the sulfomonomer residue is from 5-sodiosulfoisophthalic acid, typical sulfomonomer concentration ranges are about 4 to about 35 mole %, about 8 to about 30 mole %, and about 10 to 25 mole %, based on the total acid residues.

The sulfopolyester of our includes one or more diol residues which may include aliphatic, cycloaliphatic, and aralkyl glycols. The cycloaliphatic diols, for example, 1,3- and 1,4-cyclohexanedimethanol, may be present as their pure cis or trans isomers or as a mixture of cis and trans isomers. Non-limiting examples of lower molecular weight polyethylene glycols, e.g., wherein n is from 2 to 6, are diethylene glycol, triethylene glycol, and tetraethylene glycol. Of these lower molecular weight glycols, diethylene and triethylene glycol are most preferred. The sulfopolyester may optionally include a branching monomer. Examples of branching monomers are as described hereinabove. Further examples of branching monomer concentration ranges are from 0 to about 20 mole % and from 0 to about 10 mole %. The sulfpolyester of our novel process has a Tg of at least 25° C. Further examples of glass transition temperatures exhibited by the sulfopolyester are at least 30° C., at least 35° C., at least 40° C., at least 50° C., at least 60° C., at least 65° C., at least 80° C., and at least 90° C. Although other Tg's are possible, typical glass transition temperatures of the dry sulfopolyesters our invention are about 30° C., about 48° C., about 55° C., about 65° C., about 70° C., about 75° C., about 85° C., and about 90° C.

The water-dispersible fibers are prepared by a melt blowing process. The polymer is melted in an extruder and forced through a die. The extrudate exiting the die is rapidly attenuated to ultrafine diameters by hot, high velocity air. The orientation, rate of cooling, glass transition temperature ($T_g$), and rate of crystallization of the fiber are important because they affect the viscosity and processing properties of the polymer during attenuation. The filament is collected on a renewable surface, such as a moving belt, cylindrical drum, rotating mandrel, and so forth. Predrying of pellets (if needed), extruder zone temperature, melt temperature, screw design, throughput rate, air temperature, air flow (velocity), die air gap and set back, nose tip hole size, die temperature, die-to-collector (DCP) distance, quenching environment, collector speed, and post treatments are all factors that influence product characteristics such as filament diameters, basis weight, web thickness, pore size, softness, and shrinkage. The high velocity air also may be used to move the filaments in a somewhat random fashion that results in extensive interlacing. If a moving belt is passed under the die, a nonwoven fabric can be produced by a combination of over-lapping laydown, mechanical cohesiveness, and thermal bonding of the filaments. Overblowing onto another substrate, such as a spunbond or backing layer, is also possible. If the filaments are taken up on an rotating mandrel, a cylindrical product is formed. A water-dispersible fiber lay-down can also be prepared by the spunbond process.

The instant invention, therefore, further provides a process for water-dispersible, nonwoven fabric comprising (A) heating a water-dispersible polymer composition to a temperature above its flow point, wherein the polymer composition comprises: (i) residues of one or more dicarboxylic acids; (ii) about 4 to about 40 mole %, based on the total repeating units, of residues of at least one sulfomonomer having 2 functional groups and one or more metal sulfonate groups attached to an aromatic or cycloaliphatic ring wherein the functional groups are hydroxyl, carboxyl, or a combination thereof; (iii) one or more diol residues wherein at least 20 mole %, based on the total diol residues, is a poly(ethylene glycol) having a structure

wherein n is an integer in the range of 2 to about 500; (iv) 0 to about 25 mole %, based on the total repeating units, of residues of a branching monomer having 3 or more functional groups wherein the functional groups are hydroxyl, carboxyl, or a combination thereof; wherein the sulfopolyester has a glass transition temperature (Tg) of at least 25° C.; wherein the polymer composition contains less than 10 weight percent of a pigment or filler, based on the total weight of the polymer composition; (B) melt-spinning filaments; and (C) overlapping and collecting the filaments of Step B to form a nonwoven fabric. As described hereinabove, a water-dispersible polymer, optionally, may be blended with the sulfopolyester. In addition, a water-nondispersible polymer, optionally, may be blended with the sulfopolyester to form a blend such that blend is an immiscible blend. The dicarboxylic acid, sulfomonomer, and branching monomer residues are as described previously. The sulfopolyester has a Tg of at least 25° C. Further examples of glass transition temperatures exhibited by the sulfopolyester are at least 30° C., at least 35° C., at least 40° C., at least 50° C., at least 60° C., at least 65° C., at least 80° C., and at least 90° C. Although other Tg's are possible, typical glass transition temperatures of the dry sulfopolyesters our invention are about 30° C., about 48° C., about 55° C., about 65° C., about 70° C., about 75° C., about 85° C., and about 90° C. The invention is further illustrated by the following examples.

EXAMPLES

All pellet samples were predried under vacuum at room temperature for at least 12 hours. The dispersion times shown in Table 3 are for either complete dispersion or dissolution of the nonwoven fabric samples. The abbreviation "CE", used in Tables 2 and 3 mean "comparative example".

Example 1

A sulfopolyester containing 76 mole %, isophthalic acid, 24 mole % of sodiosulfoisophthalic acid, 76 mole % diethylene glycol, and 24 mole % 1,4-cyclohexanedimethanol with an Ih.V. of 0.29 and a Tg of 48° C. was meltblown through a nominal 6-inch die (30 holes/inch in the nosepiece) onto a cylindrical collector using the conditions shown in Table 1. Interleafing paper was not required. A soft, handleable, flexible web was obtained that did not block during the roll winding operation. Physical properties are provided in Table 2. A small piece (1"×3") of the nonwoven fabric was easily dispersed in both room temperature (RT) and 50° C. water with slight agitation as shown by data in Table 3.

TABLE 1

Melt Blowing Conditions

| Operating Condition | Typical Value |
|---|---|
| Die Configuration | |
| Die tip hole diameter | 0.0185 inches |
| Number of holes | 120 |
| Air gap | 0.060 inches |
| Set back | 0.060 inches |
| Extruder Barrel Temperatures (° F.) | |
| Zone 1 | 350 |
| Zone 2 | 510 |
| Zone 3 | 510 |
| Die Temperatures (° F.) | |
| Zone 4 | 510 |
| Zone 5 | 510 |
| Zone 6 | 510 |
| Zone 7 | 510 |
| Zone 8 | 510 |
| Air Temperatures (° F.) | |
| Furnace exit 1 | 350 |
| Furnace exit 2 | 700 |
| Furnace exit 3 | 700 |
| Die | 530-546 |
| Extrusion Conditions | |
| Air pressure | 3.0 psi |
| Melt pressure after pump | 99-113 psi |
| Take Up Conditions | |
| Throughput | 0.3 g/hole/min |
| | 0.5 g/hole/min |
| Basis weight | 36.0 g/m² |
| Collector speed | 20 ft/min |
| Collector distance | 12 inches |

TABLE 2

Physical Properties of Nonwovens

| | Filament Diameter (μm) | | | IhV (before/after) | Tg/Tm (° C.) (sulfopoly./PP) |
|---|---|---|---|---|---|
| Example | Minimum | Maximum | Average | | |
| 1 | 5 | 18 | 8.7 | 0.29/0.26 | 39/not applicable |
| 2 | 3 | 11 | 7.7 | 0.40/0.34 | 36/not applicable |
| CE 1 | 2 | 20 | 8 | Not measured | 36/163 |
| CE 2 | 4 | 10 | 7 | Not measured | 36/164 |
| CE 3 | 4 | 11 | 6 | Not measured | 35/161 |

TABLE 3

Dispersbility of Nonwovens

| Example | Water Temperature (° C.) | Initial Disintegration (minutes) | Significant Disintegration (minutes) | Complete Dispersion (minutes) |
|---|---|---|---|---|
| 1 | 23 | <0.25 | 1 | 2 |
| | 50 | <0.17 | 0.5 | 1 |
| 2 | 23 | 8 | 14 | 19 |
| | 50 | <0.5 | 5 | 8 |
| | 80 | <0.5 | 2 | 5 |
| CE 1 | 23 | 0.5 | >15 | No dispersion of PP |
| | 50 | 0.5 | >15 | No dispersion of PP |
| CE 2 | 23 | 0.5 | >15 | No dispersion of PP |
| | 50 | 0.5 | >15 | No dispersion of PP |
| CE 3 | 23 | <0.5 | 6 | No dispersion of PP |
| | 50 | <0.5 | 4 | No dispersion of PP |

Example 2

A sulfopolyester containing 89 mole %, isophthalic acid, 11 mole % of sodiosulfoisophthalic acid, 72 mole % diethylene glycol, and 28 mole % ethylene glycol with an Ih.V. of 0.4 and a Tg of 35° C. was meltblown through a 6-inch die using conditions similar to those in Table 1. A soft, handleable, flexible web was obtained that did not block during a roll winding operation. Physical properties are provided in Table 2. A small piece (1"×2") of the nonwoven fabric was easily and completely dispersed at 50° C. and 80° C.; at RT (23° C.), the fabric required a longer period of time for complete dispersion as shown by the data in Table 3.

It was found that the compositions in Examples 1 and 2 can be overblown onto other nonwoven substrates. It is also possible to condense and wrap shaped or contoured forms that are used instead of conventional web collectors. Thus, it is possible to obtain circular "roving" or plug forms of the webs.

Comparative Examples 1-3

Pellets of a sulfopolyester containing 89 mole %, isophthalic acid, 11 mole % of sodiosulfoisophthalic acid, 72 mole % diethylene glycol, and 28 mole % ethylene glycol with an Ih.V. of 0.4 and a Tg of 35° C. were combined with polypropylene (BaseII PF 008) pellets in bicomponent ratios (by wt %) of:

75 PP:25 sulfopolyester (Example 3)
50 PP:50 sulfopolyester (Example 4)
25 PP:75 sulfopolyester (Example 5)

The PP had a MFR (melt flow rate) of 800. A melt blowing operation was performed on a line equipped with a 24-inch wide die to yield handleable, soft, flexible, but nonblocking webs with the physical properties provided in Table 2. Small pieces (1"×4") of nonwoven fabric readily disintegrated as reported in Table 3. None of the fibers, however, were completely water-dispersible because of the insoluble polypropylene component.

Example 3

A circular piece (4" diameter) of the nonwoven produced in Example 2 was used as an adhesive layer between two sheets of cotton fabric. A Hannifin melt press was used to fuse the two sheets of cotton together by applying a pressure 35 psig at 200° C. for 30 seconds. The resultant assembly exhibited exceptionally strong bond strength. The cotton substrate shredded before adhesive or bond failure. Similar results have also been obtained with other cellulosics and with PET polyester substrates. Strong bonds were also produced by ultrasonic bonding techniques.

Comparative Example 4

A PP (Exxon 3356G) with a 1200 MFR was melt blown using a 24" die to yield a flexible nonwoven fabric that did not block and was easily unwound from a roll. Small pieces (1"×4") did not show any response (i.e., no disintegration or loss in basis weight) to water when immersed in water at RT or 50° C. for 15 minutes.

Example 4

Unicomponent fibers of a sulfopolyester containing 82 mole % isophthalic acid, 18 mole % of sodiosulfoisophthalic acid, 54 mole % diethylene glycol, and 46 mole % 1,4-cyclohexanedimethanol with a Tg of 55° C. were melt spun at melt temperatures of 245° C. (473° F.) on a lab staple spinning line. As-spun denier was approximately 8 d/f. Some blocking was encountered on the take-up tubes, but the 10-filament strand readily dissolved within 10-19 seconds in unagitated, demineralized water at 82° C. and a pH between 5 and 6.

Example 5

Unicomponent fibers obtained from a blend (75:25) of a sulfopolyester containing 82 mole % isophthalic acid, 18 mole % of sodiosulfoisophthalic acid, 54 mole % diethylene glycol, and 46 mole % 1,4-cyclohexanedimethanol (Tg of 55° C.) and a sulfopolyester containing 91 mole % isophthalic acid, 9 mole % of sodiosulfoisophthalic acid, 25 mole % diethylene glycol, and 75 mole % 1,4-cyclohexanedimethanol (Tg of 65° C.), respectively, were melt spun on a lab staple spinning line. The blend has a Tg of 57° C. as calculated by taking a weighted average of the Tg's of the component sulfopolyesters. The 10-filament strands did not show any blocking on the take-up tubes, but readily dissolved within 20-43 seconds in unagitated, demineralized water at 82° C. and a pH between 5 and 6.

Example 6

The blend described in Example 5 was co-spun with PET to yield bicomponent islands-in-the-sea fibers. A configuration was obtained where the sulfopolyester "sea" is 20 wt % of the fiber containing 80 wt % of PET "islands". The spun yarn elongation was 190% immediately after spinning. Blocking was not encountered as the yarn was satisfactorily unwound from the bobbins and processed a week after spinning. In a subsequent operation, the "sea" was dissolved by passing the yarn through an 88° C. soft water bath leaving only fine PET filaments.

Example 7

This prophetic example illustrates the possible application of the multicomponent and microdenier fibers of the present invention to the preparation of specialty papers. The blend described in Example 5 is co-spun with PET to yield bicomponent islands-in-the-sea fibers. The fiber contains approximately 35 wt % sulfopolyester "sea" component and approximately 65 wt % of PET "islands". The uncrimped fiber is cut to ⅛ inch lengths. In simulated papermaking, these short-cut bicomponent fibers are added to the refining operation. The sulfopolyester "sea" is removed in the agitated, aqueous slurry thereby releasing the microdenier PET fibers into the mix. At comparable weights, the microdenier PET fibers ("islands") are more effective to increase paper tensile strength than the addition of coarse PET fibers.

That which is claimed is:
1. A multicomponent fiber having a shaped cross section, comprising:
A) at least one water dispersible sulfopolyester having a glass transition temperature (Tg) of at least 57° C., said sulfopolyester comprising:
(i) residues of one or more dicarboxylic acids;
(ii) about 4 to about 40 mole %, based on the total repeating units, of residues of at least one sulfomonomer having 2 functional groups and one or more sulfonate groups attached to an aromatic or cycloaliphatic ring wherein said functional groups are hydroxyl, carboxyl, or a combination thereof;
(iii) one or more diol residues wherein at least 25 mole %, based on the total diol residues, is a poly(ethylene glycol) having a structure

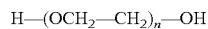

wherein n is an integer in the range of 2 to about 500; and
(iv) 0 to about 25 mole %, based on the total repeating units, of residues of a branching monomer having 3 or more functional groups wherein said functional groups are hydroxyl, carboxyl, or a combination thereof; and
B) a plurality of segments comprising at least one water non-dispersible polymer immiscible with said sulfopolyester, wherein said segments are substantially isolated from each other by said sulfopolyester intervening between said segments.

2. The multicomponent fiber according to claim 1 wherein said dicarboxylic acids are selected from aliphatic diacids, cycloaliphatic dicarboxylic acids, aromatic dicarboxylic acids, and combinations thereof.

3. The multicomponent fiber according to claim 2 in which said dicarboxylic acids are selected from succinic, glutaric, adipic, azelaic, sebacic, fumaric, maleic, itaconic, 1,3-cyclohexane dicarboxylic, 1,4-cyclohexanedicarboxylic, diglycolic, 2,5-norbornanedicarboxylic, phthalic, terephthalic, 1,4-naphthalenedicarboxylic, 2,5-naphthalenedicarboxylic, 2,6-naphthalenedicarboxylic, 2,7-naphthalenedicarboxylic, diphenic, 4,4'-oxydibenzoic, 4,4'-sulfonyldibenzoic, isophthalic, and combinations thereof.

4. The multicomponent fiber according to claim 1 wherein said sulfomonomer is a metal sulfonate salt of a sulfophthalic acid, sulfoterephthalic acid, sulfoisophthalic acid, or combinations thereof.

5. The multicomponent fiber according to claim 1 wherein said diol residues are selected from ethylene glycol, diethylene glycol, triethylene glycol, poly(ethylene) glycols, 1,3-propanediol, 2,4-dimethyl-2-ethylhexane-1,3-diol, 2,2-dimethyl-1,3-propanediol, 2-ethyl-2-butyl-1,3-propanediol, 2-ethyl-2-isobutyl-1,3-propanediol, 1,3-butanediol, 1,4-butanediol, 1,5-pentanediol, 1,6-hexanediol, 2,2,4-trimethyl-1,6-hexanediol, thiodiethanol, 1,2-cyclohexanedimethanol, 1,3-cyclohexanedimethanol, 1,4-cyclohexanedimethanol, 2,2,4,4-tetramethyl-1,3-cyclobutanediol, p-xylylenediol, and combinations thereof.

6. The multicomponent fiber according to claim 1 wherein said branching monomer is 1,1,1-trimethylol propane, 1,1,1-trimethylolethane, glycerin, pentaerythritol, erythritol, threitol, dipentaerythritol, sorbitol, trimellitic anhydride, pyromellitic dianhydride, dimethylol propionic acid, or combinations thereof.

7. The multicomponent fiber according to claim 1 wherein said water non-dispersible polymer is selected from the group consisting of polyolefins, polyesters, polyamides, polylactides, polycaprolactones, polycarbonates, polyurethanes, polyvinyl chlorides, cellulose esters, and combinations thereof.

8. The multicomponent fiber according to claim 1 wherein said water non-dispersible polymer is biodistintegratable as determined by DIN Standard 54900 or biodegradable as determined by ASTM Standard Method, D6340-98.

9. The multicomponent fiber according to claim 8 wherein said water non-dispersible polymer is an aliphatic-aromatic polyester.

10. The multicomponent fiber according to claim 1 wherein said shaped cross section is an islands-in-the-sea, segmented pie, or side by side configuration.

11. A multicomponent fiber comprising:
A) at least one water dispersible sulfopolyester having a glass transition temperature (Tg) of at least 57° C., said sulfopolyester comprising:
  (i) about 50 to about 96 mole % of one or more residues of isophthalic acid or terephthalic acid, based on the total acid residues;
  (ii) about 4 to about 30 mole %, based on the total acid residues, of a residue of sod iosulfoisophthalic acid;
  (iii) one or more diol residues wherein at least 25 mole %, based on the total diol residues, is a poly(ethylene glycol) having a structure

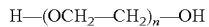

wherein n is an integer in the range of 2 to about 500;
  (iv) 0 to about 20 mole %, based on the total repeating units, of residues of a branching monomer having 3 or more functional groups wherein said functional groups are hydroxyl, carboxyl, or a combination thereof; and
(B) a plurality of segments comprising at least one water non-dispersable polymer immiscible with said sulfopolyester, wherein said segments are substantially isolated from each other by said sulfopolyester intervening between said segments;
wherein said multicomponent fiber has an islands-in-the-sea or segmented pie cross section.

12. The multicomponent fiber according to claim 11 wherein said one or more residues of isophthalic acid or terephthalic acid are present in said sulfopolyester in an amount in the range of about 75 to about 96 mole %, based on the total acid residues, and said one or more diol residues comprise about 25 to about 95 mole % of a residue of diethylene glycol, based on the total diol residues.

13. The multicomponent fiber according to claim 11 wherein said water non-dispersible polymer is selected from the group consisting of polyolefins, polyesters, polyamides, polylactides, polycaprolactones, polycarbonates, polyurethanes, polyvinyl chlorides, cellulose esters and combinations thereof.

14. The multicomponent fiber according to claim 13 wherein said water non-dispersible polymer is biodistintegratable as determined by DIN Standard 54900 or biodegradable as determined by ASTM Standard Method, D6340-98.

15. The multicomponent fiber according to claim 13 wherein said water non-dispersible polymer is an aliphatic-aromatic polyester.

16. The multicomponent fiber according to claim 1 or 11 further comprising a finish.

17. A fibrous article comprising said multicomponent fiber of any one of claim 1 or 11.

18. The fibrous article of claim 17 wherein said article is selected from the group consisting of yarns, fabrics, melt blown webs, spunbonded webs, thermobonded webs, hydroentangled webs, nonwoven fabrics, papers, multifilament fibers, nonwoven webs, textile yarns, personal care products, health care products, medical and surgical care products, laminates, fiber-containing cleaning products, replacement inserts for personal hygiene and cleaning products, packaging materials, personal protection products, laminating adhesives, protective layers, binders, and combinations thereof.

19. The fibrous article of claim 17 wherein said article comprises one or more layers of fibers.

20. The fibrous article according to claim 18 wherein said fibrous article is selected from the group consisting of wipes, gauzes, tissues, diapers, child training pants, adult incontinence briefs, adult diapers, sanitary napkins, panty liners, tampons, bandages, wound care dressings, surgical dressings, examination bed coverings, medical gowns, surgical gowns and masks, tapes, and other protective barriers.

21. The fibrous article according to claim 17 wherein said fibrous article is bonded, laminated, attached to, or used in conjunction with other materials which may or may not be water-dispersible.

22. The fibrous article according to claim 17 wherein said fibrous article is pre-moistened with at least one liquid composition and used to deliver said liquid composition to a surface.

23. The fibrous article according to claim 22 wherein said liquid composition is selected from the group consisting of detergents, wetting agents, cleaning agents, and skin care products.

24. The multicomponent fiber according to claim 1 wherein said residues of one or more dicarboxylic acids comprise residues of terephthalic acid.

25. The multicomponent fiber according to claim 24 wherein said residues of one or more dicarboxylic acids comprise residues of isophthalic acid.

26. The multicomponent fiber according to claim 24 wherein said residues of one or more dicarboxylic acids comprise about 50 to about 96 mole % of residues of terephthalic acid, based on the total acid residues.

27. The multicomponent fiber according to claim 26 wherein said residues of one or more dicarboxylic acids comprise residues of isophthalic acid.

28. The multicomponent fiber according to claim 1 wherein said sulfopolyester comprises not more than about 15 mole %, based on the total repeating units, of said residues of at least one sulfomonomer.

29. The multicomponent fiber according to claim 1 wherein said sulfopolyester comprises not more than about 10 mole %, based on the total repeating units, of said residues of at least one sulfomonomer.

30. The multicomponent fiber according to claim 1 wherein said one or more diol residues comprise ethylene glycol and diethylene glycol.

31. The multicomponent fiber according to claim 30 wherein said one or more diol residues comprise about 10 to about 75 mole % of ethylene glycol and about 25 to about 95 mole % of diethylene glycol, based on the total diol residues.

32. The multicomponent fiber according to claim 1 wherein said residues of one or more dicarboxylic acids comprise residues of isophthalic acid and residues of terephthalic acid, wherein said one or more diol residues comprise ethylene glycol residues and diethylene glycol residues.

33. The multicomponent fiber according to claim 32 wherein said residues of one or more dicarboxylic acids comprise at least about 50 mole % of residues of terephthalic acid, based on the total acid residues, wherein said one or more diol residues comprise at least about 10 mole % of ethylene glycol residues, based on the total diol residues.

34. The multicomponent fiber according to claim 33 wherein said one or more diol residues comprise at least about 40 mole % of ethylene glycol residues, based on the total diol residues, wherein said sulfopolyester comprises not more than about 10 mole %, based on the total repeating units, of said residues of at least one sulfomonomer.

35. The multicomponent fiber according to claim 1 wherein said sulfopolyester has a Tg of at least 60° C.

36. The multicomponent fiber according to claim 1 wherein said sulfopolyester has a Tg of at least 65° C.

37. The multicomponent fiber according to claim 1 wherein said sulfopolyester has a Tg of at least 60° C. to about 75° C.

38. A multicomponent fiber having a shaped cross section, consisting essentially of:

A) at least one water dispersible sulfopolyester having a glass transition temperature (Tg) of at least 57° C., said sulfopolyester comprising:
  (i) residues of one or more dicarboxylic acids;
  (ii) about 4 to about 40 mole %, based on the total repeating units, of residues of at least one sulfomonomer having 2 functional groups and one or more sulfonate groups attached to an aromatic or cycloaliphatic ring wherein said functional groups are hydroxyl, carboxyl, or a combination thereof;
  (iii) one or more diol residues wherein at least 25 mole %, based on the total diol residues, is a poly(ethylene glycol) having a structure H—(OCH$_2$—CH$_2$)$_n$—OH wherein n is an integer in the range of 2 to about 500; and
  (iv) 0 to about 25 mole %, based on the total repeating units, of residues of a branching monomer having 3 or more functional groups wherein said functional groups are hydroxyl, carboxyl, or a combination thereof; and B) a plurality of segments comprising at least one water non-dispersible polymer immiscible with said sulfopolyester, wherein said segments are substantially isolated from each other by said sulfopolyester intervening between said segments.

* * * * *